US012678236B2

(12) United States Patent
Blanchard et al.

(10) Patent No.: US 12,678,236 B2
(45) Date of Patent: Jul. 14, 2026

(54) ULTRASOUND SYSTEMS AND METHODS FOR SUSTAINED SPATIAL ATTENTION

(71) Applicant: Bard Access Systems, Inc., Salt Lake City, UT (US)

(72) Inventors: Daniel B. Blanchard, Bountiful, UT (US); Zachary S. Davis, Sandy, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 18/936,364

(22) Filed: Nov. 4, 2024

(65) Prior Publication Data

US 2025/0057604 A1 Feb. 20, 2025

Related U.S. Application Data

(63) Continuation of application No. 17/491,308, filed on Sep. 30, 2021, now Pat. No. 12,137,987.
(Continued)

(51) Int. Cl.
*A61B 34/20* (2016.01)
*A61B 8/00* (2006.01)
(Continued)

(52) U.S. Cl.
CPC ............ *A61B 34/20* (2016.02); *A61B 8/0841* (2013.01); *A61B 8/4254* (2013.01);
(Continued)

(58) Field of Classification Search
CPC ....... A61B 8/0841; A61B 8/44; A61B 8/4444; A61B 8/4455; A61B 8/46; A61B 8/461; A61B 8/462; A61B 8/463
See application file for complete search history.

(56) References Cited

U.S. PATENT DOCUMENTS 4,311,138 A 1/1982 Sugarman
4,971,068 A 11/1990 Sahi
(Continued)

FOREIGN PATENT DOCUMENTS

AU 2006201646 A1 11/2006
CN 114129137 B 9/2022
(Continued)

OTHER PUBLICATIONS

PCT/US2024/039922 filed Jul. 26, 2024 International Search Report and Written Opinion dated Jan. 9, 2025.
(Continued)

*Primary Examiner* — Serkan Akar
*Assistant Examiner* — Tommy T Ly
(74) *Attorney, Agent, or Firm* — Rutan & Tucker LLP

(57) ABSTRACT

An ultrasound probe for sustained spatial attention. The ultrasound probe can include a display screen on a visible side of the ultrasound probe, the display screen coupled to ultrasound imaging components in the ultrasound probe, the ultrasound imaging components configured to capture live subcutaneous images and render the live subcutaneous images on the display screen. The ultrasound probe can further include one or more needle trajectories depicted on the display over the live subcutaneous images, the one or more needle trajectories configured to assist a user in guided insertion of a needle into an anatomical target under the ultrasound probe. The ultrasound probe can further include a light-pattern projector on the visible side of the ultrasound probe adjacent the display screen, the light-pattern projector configured to project a light pattern corresponding to a subcutaneous depth accessible by a needle.

20 Claims, 10 Drawing Sheets

Related U.S. Application Data

(60) Provisional application No. 63/086,971, filed on Oct. 2, 2020.

(51) Int. Cl.
  *A61B 8/08*     (2006.01)
  *A61B 17/34*    (2006.01)

(52) U.S. Cl.
  CPC ............ *A61B 8/4488* (2013.01); *A61B 8/463* (2013.01); *A61B 17/3403* (2013.01); *A61B 2017/3405* (2013.01); *A61B 2034/2057* (2016.02); *A61B 2034/2065* (2016.02)

(56)                References Cited

U.S. PATENT DOCUMENTS

| | | | |
|---|---|---|---|
| 5,148,809 A | 9/1992 | Biegeleisen-Knight et al. |
| 5,181,513 A | 1/1993 | Touboul et al. |
| 5,325,293 A | 6/1994 | Dorne |
| 5,441,052 A | 8/1995 | Miyajima |
| 5,549,554 A | 8/1996 | Miraki |
| 5,573,529 A | 11/1996 | Haak et al. |
| 5,775,322 A | 7/1998 | Silverstein et al. |
| 5,879,297 A | 3/1999 | Haynor et al. |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,074,367 A | 6/2000 | Hubbell |
| 6,129,668 A | 10/2000 | Haynor et al. |
| 6,132,379 A | 10/2000 | Patacsil et al. |
| 6,216,028 B1 | 4/2001 | Haynor et al. |
| 6,233,476 B1 | 5/2001 | Strommer et al. |
| 6,245,018 B1 | 6/2001 | Lee |
| 6,263,230 B1 | 7/2001 | Haynor et al. |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,543,642 B1 | 4/2003 | Milliorn |
| 6,554,771 B1 | 4/2003 | Buil et al. |
| 6,592,520 B1 | 7/2003 | Peszynski et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,840,379 B2 | 1/2005 | Franks-Farah et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Ying et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,050,523 B2 | 11/2011 | Younge et al. |
| 8,060,181 B2 | 11/2011 | Rodriguez Ponce et al. |
| 8,068,581 B2 | 11/2011 | Boese et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,388,541 B2 | 3/2013 | Messerly et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,781,555 B2 | 7/2014 | Burnside et al. |
| 8,790,263 B2 | 7/2014 | Randall et al. |
| 8,849,382 B2 | 9/2014 | Cox et al. |
| 8,939,908 B2 | 1/2015 | Suzuki et al. |
| 8,961,420 B2 | 2/2015 | Zhang |
| 9,022,940 B2 | 5/2015 | Meier |
| 9,138,290 B2 | 9/2015 | Hadjicostis |
| 9,155,517 B2 | 10/2015 | Dunbar et al. |
| 9,204,858 B2 | 12/2015 | Pelissier et al. |
| 9,220,477 B2 | 12/2015 | Urabe et al. |
| 9,257,220 B2 | 2/2016 | Nicholls et al. |
| 9,295,447 B2 | 3/2016 | Shah |
| 9,320,493 B2 | 4/2016 | Visveshwara |
| 9,357,980 B2 | 6/2016 | Toji et al. |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,459,087 B2 | 10/2016 | Dunbar et al. |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,582,876 B2 | 2/2017 | Specht |
| 9,597,008 B2 | 3/2017 | Henkel et al. |
| 9,610,061 B2 | 4/2017 | Ebbini et al. |
| 9,636,031 B2 | 5/2017 | Cox |
| 9,649,037 B2 | 5/2017 | Lowe et al. |
| 9,649,048 B2 | 5/2017 | Cox et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 10,010,379 B1 | 7/2018 | Gibby et al. |
| 10,043,272 B2 | 8/2018 | Forzoni et al. |
| 10,380,919 B2 | 8/2019 | Savitsky et al. |
| 10,380,920 B2 | 8/2019 | Savitsky et al. |
| 10,424,225 B2 | 9/2019 | Nataneli et al. |
| 10,434,278 B2 | 10/2019 | Dunbar et al. |
| 10,449,330 B2 | 10/2019 | Newman et al. |

(56)  References Cited

U.S. PATENT DOCUMENTS

| 10,524,691 B2 | 1/2020 | Newman et al. |
| 10,636,323 B2 | 4/2020 | Buras et al. |
| 10,674,935 B2 | 6/2020 | Henkel et al. |
| 10,751,509 B2 | 8/2020 | Misener |
| 10,758,155 B2 | 9/2020 | Henkel et al. |
| 10,765,343 B2 | 9/2020 | Henkel et al. |
| 10,796,605 B2 | 10/2020 | Buras et al. |
| 10,818,199 B2 | 10/2020 | Buras et al. |
| 10,835,207 B2 | 11/2020 | Altmann et al. |
| 10,869,727 B2 | 12/2020 | Yanof et al. |
| 10,896,628 B2 | 1/2021 | Savitsky et al. |
| 11,011,078 B2 | 5/2021 | Buras et al. |
| 11,017,694 B2 | 5/2021 | Buras et al. |
| 11,017,695 B2 | 5/2021 | Buras et al. |
| 11,062,624 B2 | 7/2021 | Savitsky et al. |
| 11,120,709 B2 | 9/2021 | Savitsky et al. |
| 11,311,269 B2 | 4/2022 | Dunbar et al. |
| 11,315,439 B2 | 4/2022 | Savitsky et al. |
| 11,495,142 B2 | 11/2022 | Petrinec et al. |
| 11,600,201 B1 | 3/2023 | Savitsky et al. |
| 11,676,513 B2 | 6/2023 | Buras et al. |
| 12,062,297 B2 | 8/2024 | Buras et al. |
| 12,144,675 B2 | 11/2024 | Durfee |
| 12,396,656 B2 | 8/2025 | Durfee et al. |
| 12,414,835 B2 | 9/2025 | Gibby et al. |
| 2002/0038088 A1 | 3/2002 | Imran et al. |
| 2002/0148277 A1 | 10/2002 | Umeda |
| 2003/0028112 A1 | 2/2003 | Paladini et al. |
| 2003/0047126 A1 | 3/2003 | Tomaschko |
| 2003/0060714 A1 | 3/2003 | Henderson et al. |
| 2003/0073900 A1 | 4/2003 | Senarith et al. |
| 2003/0093001 A1 | 5/2003 | Martikainen |
| 2003/0106825 A1 | 6/2003 | Molina et al. |
| 2003/0120154 A1 | 6/2003 | Sauer et al. |
| 2003/0226868 A1* | 12/2003 | Monden ............. B65D 83/0841 |
|  |  | 225/39 |
| 2004/0055925 A1 | 3/2004 | Franks-Farah et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0013523 A1 | 1/2006 | Childlers et al. |
| 2006/0015039 A1 | 1/2006 | Cassidy et al. |
| 2006/0020204 A1 | 1/2006 | Serra et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0255475 A1 | 10/2008 | Kondrosky et al. |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0306509 A1 | 12/2009 | Pedersen et al. |
| 2010/0004539 A1* | 1/2010 | Chen ...................... A61B 8/462 |
|  |  | 600/445 |
| 2010/0020926 A1 | 1/2010 | Boese et al. |
| 2010/0106015 A1 | 4/2010 | Norris |
| 2010/0160786 A1 | 6/2010 | Nordgren et al. |
| 2010/0179428 A1 | 7/2010 | Pedersen et al. |
| 2010/0211026 A2 | 8/2010 | Sheetz et al. |
| 2010/0277305 A1 | 11/2010 | Garner et al. |
| 2010/0286515 A1 | 11/2010 | Gravenstein et al. |
| 2010/0312121 A1 | 12/2010 | Guan |
| 2011/0002518 A1 | 1/2011 | Ziv-Ari et al. |
| 2011/0071404 A1 | 3/2011 | Schmitt et al. |
| 2011/0166451 A1 | 7/2011 | Blaivas et al. |
| 2011/0288405 A1 | 11/2011 | Razavi et al. |
| 2011/0295108 A1 | 12/2011 | Cox et al. |
| 2011/0313293 A1 | 12/2011 | Lindekugel et al. |
| 2012/0136242 A1 | 5/2012 | Qi et al. |
| 2012/0179038 A1 | 7/2012 | Meurer et al. |
| 2012/0197132 A1 | 8/2012 | O'Connor |
| 2012/0209121 A1 | 8/2012 | Boudier |
| 2012/0220865 A1 | 8/2012 | Brown et al. |
| 2012/0238875 A1 | 9/2012 | Savitsky et al. |
| 2012/0277576 A1 | 11/2012 | Lui |
| 2013/0041250 A1 | 2/2013 | Pelissier et al. |
| 2013/0102889 A1* | 4/2013 | Southard .............. C08G 61/125 |
|  |  | 600/424 |
| 2013/0131499 A1 | 5/2013 | Chan et al. |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0218024 A1* | 8/2013 | Boctor ................. A61B 8/4416 |
|  |  | 600/476 |
| 2013/0296651 A1 | 11/2013 | Ito et al. |
| 2013/0324840 A1 | 12/2013 | Zhongping et al. |
| 2014/0005530 A1 | 1/2014 | Liu et al. |
| 2014/0031690 A1 | 1/2014 | Toji et al. |
| 2014/0036091 A1 | 2/2014 | Zalev et al. |
| 2014/0073976 A1 | 3/2014 | Fonte et al. |
| 2014/0100440 A1 | 4/2014 | Cheline et al. |
| 2014/0155737 A1 | 6/2014 | Manzke et al. |
| 2014/0180098 A1 | 6/2014 | Flaherty et al. |
| 2014/0187920 A1 | 7/2014 | Millett et al. |
| 2014/0188133 A1 | 7/2014 | Misener |
| 2014/0188440 A1 | 7/2014 | Donhowe et al. |
| 2014/0257104 A1 | 9/2014 | Dunbar et al. |
| 2014/0276239 A1 | 9/2014 | Sheehan |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0157295 A1 | 6/2015 | Liu et al. |
| 2015/0209113 A1 | 7/2015 | Burkholz et al. |
| 2015/0209526 A1 | 7/2015 | Matsubara et al. |
| 2015/0294497 A1 | 10/2015 | Ng et al. |
| 2015/0297097 A1 | 10/2015 | Matsubara et al. |
| 2015/0305718 A1 | 10/2015 | Ogasawara |
| 2015/0327841 A1 | 11/2015 | Banjanin et al. |
| 2015/0359991 A1 | 12/2015 | Dunbar et al. |
| 2016/0029995 A1 | 2/2016 | Navratil et al. |
| 2016/0029998 A1 | 2/2016 | Brister et al. |
| 2016/0058420 A1 | 3/2016 | Cinthio et al. |
| 2016/0074015 A1 | 3/2016 | Eda |
| 2016/0100970 A1 | 4/2016 | Brister et al. |
| 2016/0101263 A1 | 4/2016 | Blumenkranz et al. |
| 2016/0113699 A1 | 4/2016 | Sverdlik et al. |
| 2016/0120607 A1 | 5/2016 | Sorotzkin et al. |
| 2016/0143622 A1 | 5/2016 | Xie et al. |
| 2016/0157808 A1 | 6/2016 | Merritt et al. |
| 2016/0166232 A1 | 6/2016 | Merritt |
| 2016/0202053 A1 | 7/2016 | Walker et al. |
| 2016/0213398 A1* | 7/2016 | Liu ...................... A61B 8/0891 |
| 2016/0278743 A1 | 9/2016 | Kawashima |
| 2016/0278869 A1 | 9/2016 | Grunwald |
| 2016/0296208 A1 | 10/2016 | Sethuraman et al. |
| 2016/0374644 A1 | 12/2016 | Mauldin, Jr. et al. |
| 2017/0056062 A1 | 3/2017 | Buljubasic |
| 2017/0079548 A1 | 3/2017 | Silverstein et al. |
| 2017/0086785 A1 | 3/2017 | Bjaerum |
| 2017/0100092 A1 | 4/2017 | Kruse et al. |
| 2017/0164923 A1 | 6/2017 | Matsumoto |

(56) References Cited

U.S. PATENT DOCUMENTS

| 2017/0172424 A1 | 6/2017 | Eggers et al. |
| 2017/0188839 A1 | 7/2017 | Tashiro |
| 2017/0196535 A1 | 7/2017 | Arai et al. |
| 2017/0215842 A1 | 8/2017 | Ryu et al. |
| 2017/0252002 A1 | 9/2017 | Mine et al. |
| 2017/0259013 A1 | 9/2017 | Boyden et al. |
| 2017/0265840 A1 | 9/2017 | Bharat et al. |
| 2017/0303894 A1 | 10/2017 | Scully |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0220993 A1 | 8/2018 | Poland |
| 2018/0225993 A1 | 8/2018 | Buras et al. |
| 2018/0228465 A1 | 8/2018 | Southard et al. |
| 2018/0235576 A1 | 8/2018 | Brannan |
| 2018/0250078 A1 | 9/2018 | Shochat et al. |
| 2018/0272108 A1 | 9/2018 | Padilla et al. |
| 2018/0279996 A1 | 10/2018 | Cox et al. |
| 2018/0286287 A1 | 10/2018 | Razzaque |
| 2018/0310955 A1 | 11/2018 | Lindekugel et al. |
| 2018/0317881 A1 | 11/2018 | Astigarraga et al. |
| 2018/0366035 A1 | 12/2018 | Dunbar et al. |
| 2019/0060014 A1 | 2/2019 | Hazelton et al. |
| 2019/0069923 A1 | 3/2019 | Wang |
| 2019/0076121 A1 | 3/2019 | Southard et al. |
| 2019/0088019 A1 | 3/2019 | Prevrhal et al. |
| 2019/0105017 A1 | 4/2019 | Hastings |
| 2019/0117190 A1 | 4/2019 | Djajadiningrat et al. |
| 2019/0167148 A1 | 6/2019 | Durfee et al. |
| 2019/0223757 A1 | 7/2019 | Durfee |
| 2019/0223958 A1* | 7/2019 | Kohli ................... A61B 8/4427 |
| 2019/0239850 A1 | 8/2019 | Dalvin et al. |
| 2019/0282262 A1 | 9/2019 | Bouazza-Marouf et al. |
| 2019/0282324 A1 | 9/2019 | Freeman et al. |
| 2019/0298457 A1 | 10/2019 | Bharat |
| 2019/0307419 A1 | 10/2019 | Durfee |
| 2019/0307516 A1 | 10/2019 | Schotzko et al. |
| 2019/0339525 A1 | 11/2019 | Yanof et al. |
| 2019/0355278 A1 | 11/2019 | Sainsbury et al. |
| 2019/0365348 A1 | 12/2019 | Toume et al. |
| 2020/0041261 A1 | 2/2020 | Bernstein et al. |
| 2020/0069285 A1 | 3/2020 | Annangi et al. |
| 2020/0069929 A1 | 3/2020 | Mason et al. |
| 2020/0113540 A1 | 4/2020 | Gijsbers et al. |
| 2020/0129136 A1 | 4/2020 | Harding et al. |
| 2020/0188028 A1 | 6/2020 | Feiner et al. |
| 2020/0230391 A1 | 7/2020 | Burkholz et al. |
| 2020/0305927 A1* | 10/2020 | Grim ................... A61B 8/4444 |
| 2020/0367860 A1 | 11/2020 | Rouet et al. |
| 2021/0007710 A1 | 1/2021 | Douglas |
| 2021/0045716 A1 | 2/2021 | Shiran et al. |
| 2021/0161612 A1 | 6/2021 | Black et al. |
| 2021/0166583 A1 | 6/2021 | Buras et al. |
| 2021/0307838 A1 | 10/2021 | Xia et al. |
| 2021/0327303 A1 | 10/2021 | Buras et al. |
| 2021/0353255 A1 | 11/2021 | Schneider et al. |
| 2021/0402144 A1 | 12/2021 | Messerly |
| 2022/0022969 A1 | 1/2022 | Misener |
| 2022/0031965 A1 | 2/2022 | Durfee |
| 2022/0039685 A1 | 2/2022 | Misener et al. |
| 2022/0039777 A1 | 2/2022 | Durfee |
| 2022/0054108 A1 | 2/2022 | In 'T Groen et al. |
| 2022/0096797 A1 | 3/2022 | Prince |
| 2022/0104886 A1 | 4/2022 | Blanchard et al. |
| 2022/0117582 A1 | 4/2022 | Mclaughlin et al. |
| 2022/0160434 A1 | 5/2022 | Messerly et al. |
| 2022/0168050 A1 | 6/2022 | Sowards et al. |
| 2022/0172354 A1 | 6/2022 | Misener et al. |
| 2022/0211442 A1 | 7/2022 | McLaughlin et al. |
| 2022/0354462 A1 | 11/2022 | Southworth et al. |
| 2022/0381630 A1 | 12/2022 | Sowards et al. |
| 2022/0401157 A1 | 12/2022 | Sowards et al. |
| 2023/0053189 A1 | 2/2023 | Geric et al. |
| 2023/0113291 A1 | 4/2023 | de Wild et al. |
| 2023/0240643 A1 | 8/2023 | Cermak et al. |
| 2023/0389893 A1 | 12/2023 | Misener et al. |
| 2024/0008929 A1 | 1/2024 | Misener et al. |
| 2024/0050060 A1 | 2/2024 | Kadokura et al. |
| 2024/0050061 A1 | 2/2024 | McLaughlin et al. |
| 2024/0058074 A1 | 2/2024 | Misener |
| 2024/0062678 A1 | 2/2024 | Sowards et al. |
| 2025/0000488 A1 | 1/2025 | Misener et al. |
| 2025/0032152 A1 | 1/2025 | Miller et al. |
| 2025/0064425 A1 | 2/2025 | Durfee |
| 2025/0143804 A1 | 5/2025 | Misener |
| 2025/0176942 A1 | 6/2025 | McLaughlin et al. |
| 2025/0339174 A1 | 11/2025 | Durfee et al. |

FOREIGN PATENT DOCUMENTS

| EP | 0933063 A1 | 8/1999 |
| EP | 1504713 A1 | 2/2005 |
| EP | 1591074 B1 | 5/2008 |
| EP | 3181083 A1 | 6/2017 |
| EP | 3530221 A1 | 8/2019 |
| JP | 2000271136 A | 10/2000 |
| JP | 2014150928 A | 8/2014 |
| JP | 2018175547 A | 11/2018 |
| KR | 20180070878 A | 6/2018 |
| KR | 20190013133 A | 2/2019 |
| KR | 20220141308 A | 10/2022 |
| WO | 2013059714 A1 | 4/2013 |
| WO | 2014115150 A1 | 7/2014 |
| WO | 2014174305 A2 | 10/2014 |
| WO | 2015017270 A1 | 2/2015 |
| WO | 2017096487 A1 | 6/2017 |
| WO | 2017214428 A1 | 12/2017 |
| WO | 2018026878 A1 | 2/2018 |
| WO | 2018134726 A1 | 7/2018 |
| WO | 2018206473 A1 | 11/2018 |
| WO | 2019232451 A1 | 12/2019 |
| WO | 2020002620 A1 | 1/2020 |
| WO | 2020016018 A1 | 1/2020 |
| WO | 2019232454 A9 | 2/2020 |
| WO | 2020044769 A1 | 3/2020 |
| WO | 2020102665 A1 | 5/2020 |
| WO | 2020186198 A1 | 9/2020 |
| WO | 2022031762 A1 | 2/2022 |
| WO | 2022072727 A2 | 4/2022 |
| WO | 2022081904 A1 | 4/2022 |
| WO | 2022203713 A2 | 9/2022 |
| WO | 2022263763 A1 | 12/2022 |
| WO | 2023235435 A1 | 12/2023 |
| WO | 2024010940 A1 | 1/2024 |
| WO | 2024039608 A1 | 2/2024 |
| WO | 2024039719 A1 | 2/2024 |
| WO | 2025024821 A1 | 1/2025 |
| WO | 2025231303 A1 | 11/2025 |

OTHER PUBLICATIONS

U.S. Appl. No. 17/478,754, filed Sep. 17, 2021 Non-Final Office Action dated Dec. 30, 2024.

U.S. Appl. No. 17/888,359, filed Aug. 15, 2022 Non-Final Office Action dated Feb. 12, 2025.

EZono, eZSimulator, https://www.ezono.com/en/ezsimulator/, last accessed Sep. 13, 2022.

Ikhsan Mohammad et al: "Assistive technology for ultrasound-guided central venous catheter placement", Journal of Medical Ultrasonics, Japan Society of Ultrasonics in Medicine, Tokyo, JP, vol. 45, No. 1, Apr. 19, 2017, pp. 41-57, XPO36387340, ISSN: 1346-4523, DOI: 10.1007/S10396-017-0789-2 [retrieved on Apr. 19, 2017].

Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).

(56) References Cited

OTHER PUBLICATIONS

Pagoulatos, N. et al. "New spatial localizer based on fiber optics with applications in 3D ultrasound imaging" Proceeding of Spie, vol. 3976 (Apr. 18, 2000; Apr. 18, 2000).

PCT/US2021/042369 filed Jul. 20, 2021 International Search Report and Written Opinion dated Oct. 25, 2021.

PCT/US2021/044419 filed Aug. 3, 2021 International Search Report and Written Opinion dated Nov. 19, 2021.

PCT/US2021/045218 filed Aug. 9, 2021 International Search Report and Written Opinion dated Nov. 23, 2021.

PCT/US2021/050973 filed Sep. 17, 2021 International Search Report and Written Opinion dated Nov. 7, 2022.

PCT/US2021/053018 filed Sep. 30, 2021 International Search Report and Written Opinion dated May 3, 2022.

PCT/US2021/055076 filed Oct. 14, 2021 International Search Report and Written Opinion dated Mar. 25, 2022.

PCT/US2023/024067 filed May 31, 2023 International Search Report and Written Opinion dated Sep. 15, 2023.

PCT/US2023/027147 filed Jul. 7, 2023 International Search Report and Written Opinion dated Oct. 2, 2023.

PCT/US2023/030160 filed Aug. 14, 2023 International Search Report and Written Opinion dated Oct. 23, 2023.

PCT/US2023/030347 filed Aug. 16, 2023 International Search Report and Written Opinion dated Nov. 6, 2023.

Practical guide for safe central venous catheterization and management 2017 Journal of Anesthesia vol. 34 published online Nov. 30, 2019 pp. 167-186.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.

Sonosim, https://sonosim.com/ultrasound-simulation/? last accessed Sep. 13, 2022.

State, A., et al. (Aug. 1996). Technologies for augmented reality systems: Realizing ultrasound-guided needle biopsies. In Proceedings of the 23rd annual conference on computer graphics and interactive techniques (pp. 439-446) (Year: 1996).

Stolka, P.J., et al., (2014). Needle Guidance Using Handheld Stereo Vision and Projection for Ultrasound-Based Interventions. In: Galland, P., Hata, N., Barillot, C., Hornegger, J., Howe, R. (eds) Medical Image Computing and Computer-Assisted Intervention—MICCAI 2014. MICCAI 2014. (Year: 2014).

U.S. Appl. No. 17/380,767, filed Jul. 20, 2021 Non-Final Office Action dated Mar. 6, 2023.

U.S. Appl. No. 17/380,767, filed Jul. 20, 2021 Notice of Allowance dated Aug. 31, 2023.

U.S. Appl. No. 17/380,767, filed Jul. 20, 2021 Restriction Requirement dated Dec. 15, 2022.

U.S. Appl. No. 17/393,283, filed Aug. 3, 2021 Advisory Action dated Jan. 19, 2024.

U.S. Appl. No. 17/393,283, filed Aug. 3, 2021 Final Office Action dated Oct. 16, 2023.

U.S. Appl. No. 17/393,283, filed Aug. 3, 2021 Non-Final Office Action dated Feb. 29, 2024.

U.S. Appl. No. 17/393,283, filed Aug. 3, 2021 Non-Final Office Action dated Mar. 31, 2023.

U.S. Appl. No. 17/393,283, filed Aug. 3, 2021 Notice of Allowance dated Sep. 18, 2024.

U.S. Appl. No. 17/393,283, filed Aug. 3, 2021 Restriction Requirement dated Jan. 12, 2023.

U.S. Appl. No. 17/397,486, filed Aug. 9, 2021 Advisory Action dated Oct. 5, 2023.

U.S. Appl. No. 17/397,486, filed Aug. 9, 2021 Final Office Action dated Aug. 4, 2023.

U.S. Appl. No. 17/397,486, filed Aug. 9, 2021 Non-Final Office Action dated Jan. 23, 2023.

U.S. Appl. No. 17/397,486, filed Aug. 9, 2021 Non-Final Office Action dated Mar. 1, 2024.

U.S. Appl. No. 17/397,486, filed Aug. 9, 2021 Notice of Allowance dated Jul. 10, 2024.

U.S. Appl. No. 17/397,486, filed Aug. 9, 2021 Restriction Requirement dated Aug. 12, 2022.

U.S. Appl. No. 17/478,754, filed Sep. 17, 2021 Non-Final Office Action dated Jul. 1, 2024.

U.S. Appl. No. 17/478,754, filed Sep. 17, 2021 Restriction Requirement dated Jan. 22, 2024.

U.S. Appl. No. 17/491,308, filed Sep. 30, 2021 Board Decision dated Oct. 25, 2023.

U.S. Appl. No. 17/491,308, filed Sep. 30, 2021 Board Decison dated Oct. 25, 2023.

U.S. Appl. No. 17/491,308, filed Sep. 30, 2021 Final Office Action dated Aug. 29, 2023.

U.S. Appl. No. 17/491,308, filed Sep. 30, 2021 Non-Final Office Action dated Jun. 5, 2023.

U.S. Appl. No. 17/491,308, filed Sep. 30, 2021 Non-Final Office Action dated Mar. 22, 2024.

U.S. Appl. No. 17/491,308, filed Sep. 30, 2021 Notice of Allowance dated Jun. 27, 2024.

U.S. Appl. No. 17/491,308, filed Sep. 30, 2021 Restriction Requirement dated Feb. 27, 2023.

U.S. Appl. No. 17/501,909, filed Oct. 14, 2021 Advisory Action dated Jan. 24, 2024.

U.S. Appl. No. 17/501,909, filed Oct. 14, 2021 Final Office Action dated Aug. 5, 2024.

U.S. Appl. No. 17/501,909, filed Oct. 14, 2021 Final Office Action dated Nov. 21, 2023.

U.S. Appl. No. 17/501,909, filed Oct. 14, 2021 Non-Final Office Action dated Jun. 6, 2023.

U.S. Appl. No. 17/501,909, filed Oct. 14, 2021 Non-Final Office Action dated Mar. 21, 2024.

U.S. Appl. No. 17/501,909, filed Oct. 14, 2021 Notice of Allowance dated Sep. 25, 2024.

U.S. Appl. No. 17/501,909, filed Oct. 14, 2021 Restriction Requirement dated Feb. 1, 2023.

U.S. Appl. No. 17/832,389, filed Jun. 3, 2022 Advisory Action dated Apr. 4, 2024.

U.S. Appl. No. 17/832,389, filed Jun. 3, 2022 Final Office Action dated Jan. 25, 2024.

U.S. Appl. No. 17/832,389, filed Jun. 3, 2022 Non-Final Office Action dated Oct. 6, 2023.

U.S. Appl. No. 17/832,389, filed Jun. 3, 2022 Notice of Allowance dated May 15, 2024.

U.S. Appl. No. 17/832,389, filed Jun. 3, 2022 Restriction Requirement dated Jul. 13, 2023.

U.S. Appl. No. 17/861,031, filed Jul. 8, 2022 Advisory Action dated Jun. 7, 2024.

U.S. Appl. No. 17/861,031, filed Jul. 8, 2022 Final Office Action dated Mar. 15, 2024.

U.S. Appl. No. 17/861,031, filed Jul. 8, 2022 Non-Final Office Action dated Sep. 14, 2023.

U.S. Appl. No. 17/861,031, filed Jul. 8, 2022 Notice of Allowance dated Jul. 3, 2024.

U.S. Appl. No. 17/888,359, filed Aug. 15, 2022 Restriction Requirement dated Sep. 5, 2024.

U.S. Appl. No. 18/385,101, filed Oct. 30, 2023 Notice of Allowance dated Aug. 20, 2024.

William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

Manuel Birlo et al: "Utility of Optical See-Through Head Mounted Displays in Augmented Reality-Assisted Surgery: A systematic review", arxiv.org, Cornell University Library, 201 OLIN Library Cornell University Ithaca, NY 14853, Feb. 8, 2022 (Feb. 8, 2022), XP091157128, DOI: 10.1016/J.MEDIA.2022.102361 Section 8.5, section 8.2.

PCT/US2025/027390 filed May 1, 2025 International Search Report and Written Opinion dated Jul. 29, 2025.

U.S. Appl. No. 17/478,754, filed Sep. 17, 2021 Advisory Action dated Jun. 24, 2025.

U.S. Appl. No. 17/478,754, filed Sep. 17, 2021 Final Office Action dated Apr. 11, 2025.

(56)                     References Cited

OTHER PUBLICATIONS

U.S. Appl. No. 17/888,359, filed Aug. 15, 2022 Final Office Action dated Jun. 18, 2025.
U.S. Appl. No. 17/478,754, filed Sep. 17, 2021 Notice of Allowance dated Aug. 14, 2025.
U.S. Appl. No. 17/888,359, filed Aug. 15, 2022 Advisory Action dated Sep. 3, 2025.
U.S. Appl. No. 17/888,359, filed Aug. 15, 2022 Notice of Allowance dated Oct. 21, 2025.
U.S. Appl. No. 17/890,148, filed Aug. 17, 2022 Final Office Action dated Jan. 29, 2026.
U.S. Appl. No. 17/890,148, filed Aug. 17, 2022 Non-Final Office Action dated Sep. 9, 2025.
U.S. Appl. No. 18/652,728, filed May 1, 2024 Non-Final Office Action dated Oct. 1, 2025.
U.S. Appl. No. 18/786,361, filed Jul. 26, 2024 Non-Final Office Action dated Jan. 28, 2026.
U.S. Appl. No. 18/885,090, filed Sep. 13, 2024 Non-Final Office Action dated Sep. 29, 2025.
U.S. Appl. No. 17/890,148, filed Aug. 17, 2022 Notice of Allowance dated Apr. 21, 2026.
U.S. Appl. No. 18/652,728, filed May 1, 2024 Final Office Action dated Apr. 3, 2026.
U.S. Appl. No. 18/885,090, filed Sep. 13, 2024 Notice of Allowance dated Mar. 10, 2026.
U.S. Appl. No. 19/019,042, filed Jan. 13, 2025 Notice of Allowance dated Feb. 4, 2026.
U.S. Appl. No. 19/043,025, filed Jan. 31, 2025 Non-Final Office Action dated Apr. 7, 2026.

* cited by examiner

ULTRASOUND SYSTEMS AND METHODS FOR SUSTAINED SPATIAL ATTENTION

PRIORITY

This application is a continuation of U.S. patent application Ser. No. 17/491,308, filed Sep. 30, 2021, now U.S. Pat. No. 12,137,987, which claims the benefit of priority to U.S. Provisional Application No. 63/086,971, filed Oct. 2, 2020, each of which is incorporated by reference in its entirety into this application.

BACKGROUND

A variety of ultrasound systems exist including wired or wireless ultrasound probes for ultrasound imaging. Whether wired or wireless, an ultrasound system such as the foregoing requires a clinician to switch his or her spatial attention between different spatial regions, particularly between 1) a relatively close ultrasound probe being used for ultrasound imaging and 2) a relatively distant display rendering corresponding ultrasound images. Having to switch spatial attention between the ultrasound probe and the display can be difficult when ultrasound imaging and attempting to simultaneously establish an insertion site with a needle, place a vascular access device ("VAD") such as a catheter in a blood vessel of a patient at the insertion site, or the like. Such difficulties can be pronounced for less experienced clinicians, older clinicians having reduced lens flexibility in their eyes, etc. Ultrasound systems are needed that do not require clinicians to continuously switch their spatial attention between different spatial regions.

Disclosed herein are ultrasound systems and methods for sustained spatial attention in one or more spatial regions.

SUMMARY

Disclosed herein is an ultrasound probe including, in some embodiments, a probe body, a probe head extending from a distal end of the probe body, and a camera integrated into a side of the ultrasound probe. The probe head includes a plurality of ultrasonic transducers arranged in an array. The camera is configured for recording one or more still or moving images of a procedural field with a depth of field including a plane of a distal end of the probe head and a field of view including a spatial region about the probe head.

In some embodiments, the ultrasound probe further includes a light-pattern projector integrated into the side of the ultrasound probe including the camera. The light-pattern projector is configured to project a light pattern in the spatial region about the probe head focused in the plane of the distal end of the probe head. The light pattern is configured for guided insertion of a needle into an anatomical target under the probe head in the procedural field.

In some embodiments, the light pattern includes periodic hash marks along one or more rays radiating from a central axis of the ultrasound probe in the plane of the probe head. Each hash mark of the hash marks corresponds to a depth under the probe head accessible by the needle along an associated ray at a needle-insertion angle with respect to the plane of the probe head.

In some embodiments, the light pattern includes periodic concentric circular arcs bound between two or more rays radiating from a central axis of the ultrasound probe in the plane of the probe head. Each circular arc of the circular arcs corresponds to a depth under the probe head accessible by the needle along an associated ray at a needle-insertion angle with respect to the plane of the probe head.

In some embodiments, the ultrasound probe further includes a needle-guide holder extending from a side of the probe head in common with the side of the ultrasound probe including the camera.

In some embodiments, the ultrasound probe further includes a single-use needle guide coupled to the needle-guide holder. The needle-guide holder, the needle guide, or a combination of the needle-guide holder and the needle guide includes at least one degree of freedom enabling the needle guide to swivel between sides of the ultrasound probe.

Also disclosed herein is an ultrasound system including, in some embodiments, a console and an ultrasound probe. The console includes a display configured to render on a display screen thereof ultrasound images and one or more still or moving images of a procedural field. The ultrasound probe includes a probe body, a probe head extending from a distal end of the probe body, and a camera integrated into a side of the ultrasound probe. The probe head includes a plurality of ultrasonic transducers arranged in an array. The camera is configured for recording the one-or-more still or moving images of the procedural field with a depth of field including a plane of a distal end of the probe head and a field of view including a spatial region about the probe head.

In some embodiments, the ultrasound probe further includes a needle-guide holder extending from a side of the probe head in common with the side of the ultrasound probe including the camera.

In some embodiments, the ultrasound probe further includes a single-use needle guide coupled to the needle-guide holder. The needle-guide holder, the needle guide, or a combination of the needle-guide holder and the needle guide includes at least one degree of freedom enabling the needle guide to swivel between sides of the ultrasound probe.

In some embodiments, the ultrasound probe further includes a light-pattern projector integrated into the side of the ultrasound probe including the camera. The light-pattern projector is configured to project a light pattern in the spatial region about the probe head focused in the plane of the distal end of the probe head. The light pattern is configured for guided insertion of a needle into an anatomical target under the probe head in the procedural field.

In some embodiments, the light pattern includes periodic hash marks along one or more rays radiating from a central axis of the ultrasound probe in the plane of the probe head. Each hash mark of the hash marks corresponds to a depth under the probe head accessible by the needle along an associated ray at a needle-insertion angle with respect to the plane of the probe head.

In some embodiments, the light pattern includes periodic concentric circular arcs bound between two or more rays radiating from a central axis of the ultrasound probe in the plane of the probe head. Each circular arc of the circular arcs corresponds to a depth under the probe head accessible by the needle along an associated ray at a needle-insertion angle with respect to the plane of the probe head.

In some embodiments, the one-or-more still or moving images show both the light pattern in the spatial region about the probe head and the needle in relation to the light pattern when both the light pattern and the needle are present in the spatial region about the probe head. The one-or-more still or moving images show both the light pattern and the needle in relation to the light pattern for the guided insertion of the needle into the anatomical target under the probe head optionally on the display.

In some embodiments, the display is further configured to render on the display screen one or more overlying needle trajectories lying over the ultrasound images in accordance with one or more depths accessible by the needle indicated by the light pattern. The one-or-more overlying needle trajectories are configured for the guided insertion of the needle into the anatomical target under the probe head on the display.

In some embodiments, the display is further configured to render on the display screen an overlying pattern lying over the one-or-more still or moving images. The overlying pattern is configured for guided insertion of a needle into an anatomical target under the probe head on the display.

In some embodiments, the overlying pattern includes periodic hash marks along one or more rays radiating from a central axis of the ultrasound probe in the plane of the probe head. Each hash mark of the hash marks corresponds to a depth under the probe head accessible by the needle along an associated ray at a needle-insertion angle with respect to the plane of the probe head.

In some embodiments, the overlying pattern includes periodic concentric circular arcs bound between two or more rays radiating from a central axis of the ultrasound probe in the plane of the probe head. Each circular arc of the circular arcs corresponds to a depth under the probe head accessible by the needle along an associated ray at a needle-insertion angle with respect to the plane of the probe head.

In some embodiments, the one-or-more still or moving images show the needle in relation to the overlying pattern when the needle is present in the spatial region about the probe head. The one-or-more still or moving images show the needle in relation to the overlying pattern for the guided insertion of the needle into the anatomical target under the probe head optionally on the display.

In some embodiments, the display is further configured to render on the display screen one or more overlying needle trajectories lying over the ultrasound images in accordance with one or more depths accessible by the needle indicated by the overlying pattern. The one-or-more overlying needle trajectories are configured for the guided insertion of the needle into an anatomical target under the probe head on the display.

Also disclosed herein is an ultrasound probe including, in some embodiments, a probe body, a probe head extending from a distal end of the probe body, and a display integrated into a side of the ultrasound probe. The probe head includes a plurality of ultrasonic transducers arranged in an array. The display is configured to render on a display screen thereof ultrasound images and one or more overlying needle trajectories lying over the ultrasound images. The one-or-more overlying needle trajectories are configured for guided insertion of a needle into an anatomical target under the probe head on the display.

In some embodiments, the ultrasound probe further includes a light-pattern projector integrated into the side of the ultrasound probe including the display. The light-pattern projector is configured to project a light pattern in a spatial region about the probe head focused in a plane of a distal end of the probe head. The light pattern is configured for the guided insertion of the needle into the anatomical target under the probe head in the procedural field.

In some embodiments, the light pattern includes periodic hash marks along one or more rays radiating from a central axis of the ultrasound probe in the plane of the probe head.

Each hash mark of the hash marks corresponds to a depth under the probe head accessible by the needle along an associated ray at a needle-insertion angle with respect to the plane of the probe head.

In some embodiments, the light pattern includes periodic concentric circular arcs bound between two or more rays radiating from a central axis of the ultrasound probe in the plane of the probe head. Each circular arc of the circular arcs corresponds to a depth under the probe head accessible by the needle along an associated ray at a needle-insertion angle with respect to the plane of the probe head.

In some embodiments, the one-or-more overlying needle trajectories lying over the ultrasound images are in accordance with one or more depths accessible by the needle indicated by the light pattern.

In some embodiments, the ultrasound probe further includes a needle-guide holder extending from the side of the ultrasound probe including the display.

In some embodiments, the ultrasound probe further includes a single-use needle guide coupled to the needle-guide holder. The needle-guide holder, the needle guide, or a combination of the needle-guide holder and the needle guide includes at least one degree of freedom enabling the needle guide to swivel between sides of the ultrasound probe.

Also disclosed herein is a method of an ultrasound system including, in some embodiments, an ultrasound probe-obtaining step, an ultrasound probe-moving step, a recording step, an ultrasound image-monitoring step, and a needle-inserting step. The ultrasound probe-obtaining step includes obtaining an ultrasound probe. The ultrasound probe includes a probe body, a probe head extending from a distal end of the probe body, and a camera integrated into a side of the ultrasound probe. The ultrasound probe-moving step includes moving the ultrasound probe over a patient while the ultrasound probe emits generated ultrasound signals into the patient from ultrasonic transducers in the probe head and receives reflected ultrasound signals from the patient by the ultrasonic transducers. The recording step includes recording one or more still or moving images of a procedural field with a depth of field including a plane of a distal end of the probe head and a field of view including a spatial region about the probe head. The ultrasound image-monitoring step includes monitoring ultrasound images rendered on a display screen of a display associated with a console of the ultrasound system to identify an anatomical target of the patient under the probe head. The needle-inserting step includes inserting a needle into the anatomical target. Optionally, the inserting of the needle is guided by the display with reference to the one-or-more still or moving images rendered on the display screen thereof.

In some embodiments, the method further includes a needle guide-attaching step. The needle guide-attaching step includes attaching a needle guide to a needle-guide holder extending from the probe body. The needle guide includes a needle through hole configured to direct the needle into the patient under the probe head at a needle-insertion angle with respect to the plane of the probe head.

In some embodiments, the method further includes a needle guide-swiveling step. The needle guide-swiveling step includes swiveling the needle guide between sides of the ultrasound probe to find a suitable needle trajectory before the needle-inserting step. The needle-guide holder, the needle guide, or a combination of the needle-guide holder and the needle guide includes at least one degree of freedom enabling the swiveling of the needle guide.

In some embodiments, the needle is guided in the procedural field during the needle-inserting step in accordance with a light pattern in the spatial region about the probe head. The light pattern is projected from a light-pattern projector integrated into the side of the ultrasound probe including the camera and focused in the plane of the distal end of the probe head for guiding the needle in the procedural field.

In some embodiments, the light pattern includes periodic hash marks along one or more rays radiating from a central axis of the ultrasound probe in the plane of the probe head. Each hash mark of the hash marks corresponds to a depth under the probe head accessible by the needle along an associated ray at a needle-insertion angle with respect to the plane of the probe head.

In some embodiments, the light pattern includes periodic concentric circular arcs bound between two or more rays radiating from a central axis of the ultrasound probe in the plane of the probe head. Each circular arc of the circular arcs corresponds to a depth under the probe head accessible by the needle along an associated ray at a needle-insertion angle with respect to the plane of the probe head.

In some embodiments, the needle is further guided on the display during the needle-inserting step. The one-or-more still or moving images show both the light pattern in the spatial region about the probe head and the needle in relation to the light pattern for guiding the needle on the display.

In some embodiments, the needle is further guided on the display during the needle-inserting step. The ultrasound images show one or more overlying needle trajectories in accordance with one or more depths accessible by the needle indicated by the light pattern for guiding the needle on the display.

In some embodiments, the needle is guided on the display during the needle-inserting step in accordance with an overlying pattern rendered over the one-or-more still or moving images on the display screen for guiding the needle on the display.

In some embodiments, the overlying pattern includes periodic hash marks along one or more rays radiating from a central axis of the ultrasound probe in the plane of the probe head. Each hash mark of the hash marks corresponds to a depth under the probe head accessible by the needle along an associated ray at a needle-insertion angle with respect to the plane of the probe head.

In some embodiments, the overlying pattern includes periodic concentric circular arcs bound between two or more rays radiating from a central axis of the ultrasound probe in the plane of the probe head. Each circular arc of the circular arcs corresponds to a depth under the probe head accessible by the needle along an associated ray at a needle-insertion angle with respect to the plane of the probe head.

In some embodiments, the needle is further guided on the display during the needle-inserting step. The ultrasound images show one or more overlying needle trajectories in accordance with one or more depths accessible by the needle indicated by the overlying pattern for guiding the needle on the display.

These and other features of the concepts provided herein will become more apparent to those of skill in the art in view of the accompanying drawings and following description, which describe particular embodiments of such concepts in greater detail.

DESCRIPTION

Figure 1:
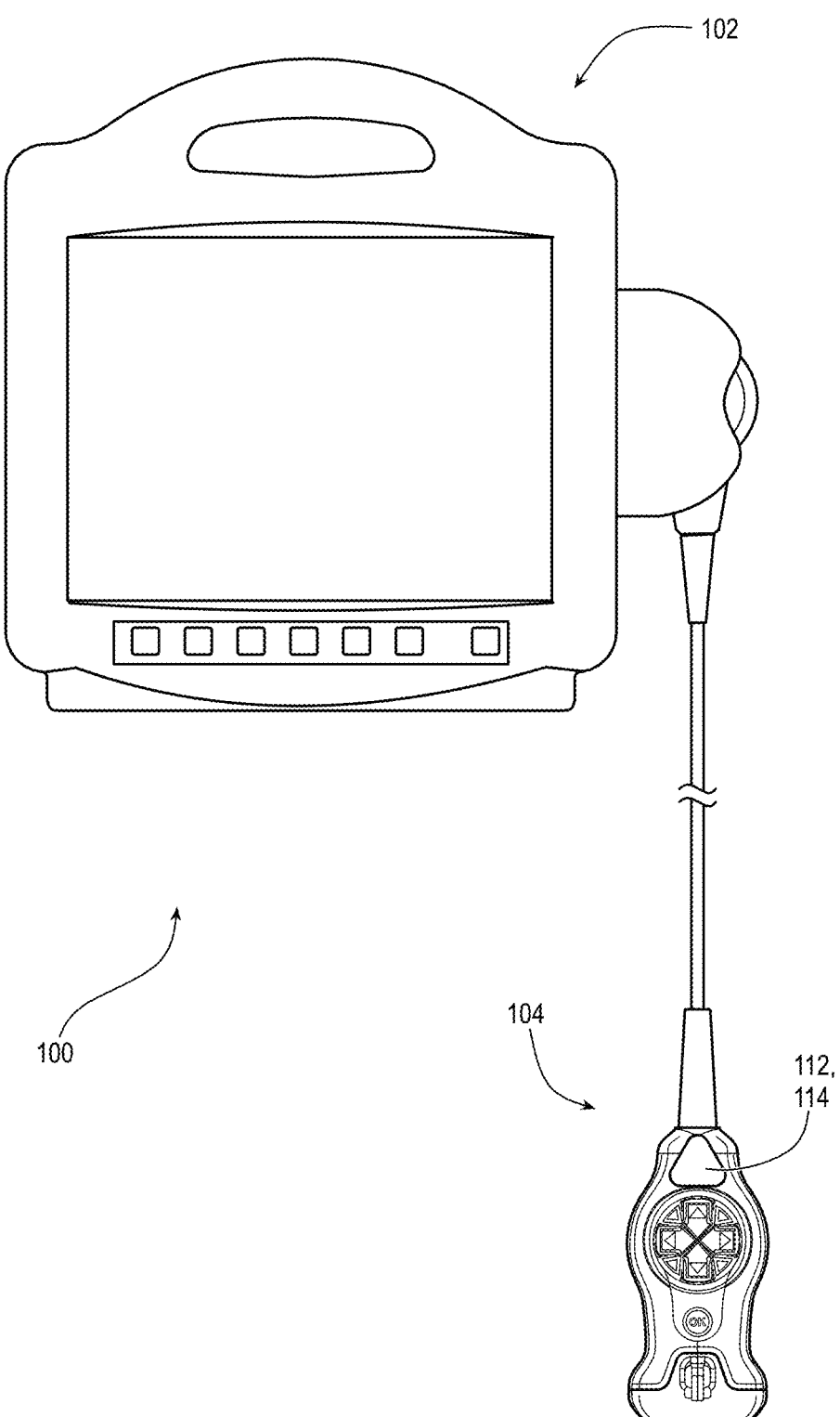
FIG. 1 illustrates an ultrasound system with a first ultrasound probe in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or "proximal section" of, for example, a catheter includes a portion or section of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal section, or the proximal length of the catheter can include the proximal end of the catheter; however, the proximal portion, the proximal section, or the proximal length of the catheter need not include the proximal end of the catheter. That is, unless context suggests otherwise, the proximal portion, the proximal section, or the proximal length of the catheter is not a terminal portion or terminal length of the catheter.

With respect to "distal," a "distal portion" or a "distal section" of, for example, a catheter includes a portion or section of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal section, or the distal length of the catheter can include the distal end of the catheter; however, the distal portion, the distal section, or the distal length of the catheter need not include the distal end of the catheter. That is, unless context suggests otherwise, the distal portion, the distal section, or the distal length of the catheter is not a terminal portion or terminal length of the catheter.

Unless defined otherwise, all technical and scientific terms used herein have the same meaning as commonly understood by those of ordinary skill in the art.

As set forth above, a variety of ultrasound systems exist including wired or wireless ultrasound probes for ultrasound imaging. Whether wired or wireless, an ultrasound system such as the foregoing requires a clinician to switch his or her spatial attention between different spatial regions, particularly between 1) a relatively close ultrasound probe being used for ultrasound imaging and 2) a relatively distant display rendering corresponding ultrasound images. Having to switch spatial attention between the ultrasound probe and the display can be difficult when ultrasound imaging and attempting to simultaneously establish an insertion site with a needle, place a VAD such as a catheter in a blood vessel of a patient at the insertion site, or the like. Such difficulties can be pronounced for less experienced clinicians, older clinicians having reduced lens flexibility in their eyes, etc. Ultrasound systems are needed that do not require clinicians to continuously switch their spatial attention between different spatial regions.

Disclosed herein are ultrasound systems and methods for sustained spatial attention. For example, an ultrasound system can include a console and an ultrasound probe. A display of the console can be configured to display ultrasound images and one or more still or moving images of a procedural field. The ultrasound probe can include a camera integrated into the ultrasound probe for recording the one-or-more still or moving images of the procedural field with a depth of field including a distal end of a probe head and a field of view including a spatial region about the probe head. With the one-or-more still or moving images displayed along with the ultrasound images, a clinician need not switch his or her spatial attention between spatial regions such as the procedural field and the display quite as frequently as with existing ultrasound systems, thereby sustaining spatial attention in one or more spatial regions. These and other features will become more apparent to those of skill in the art in view of the accompanying drawings and following description, which describe particular embodiments in greater detail.

Ultrasound Systems

Figure 3:
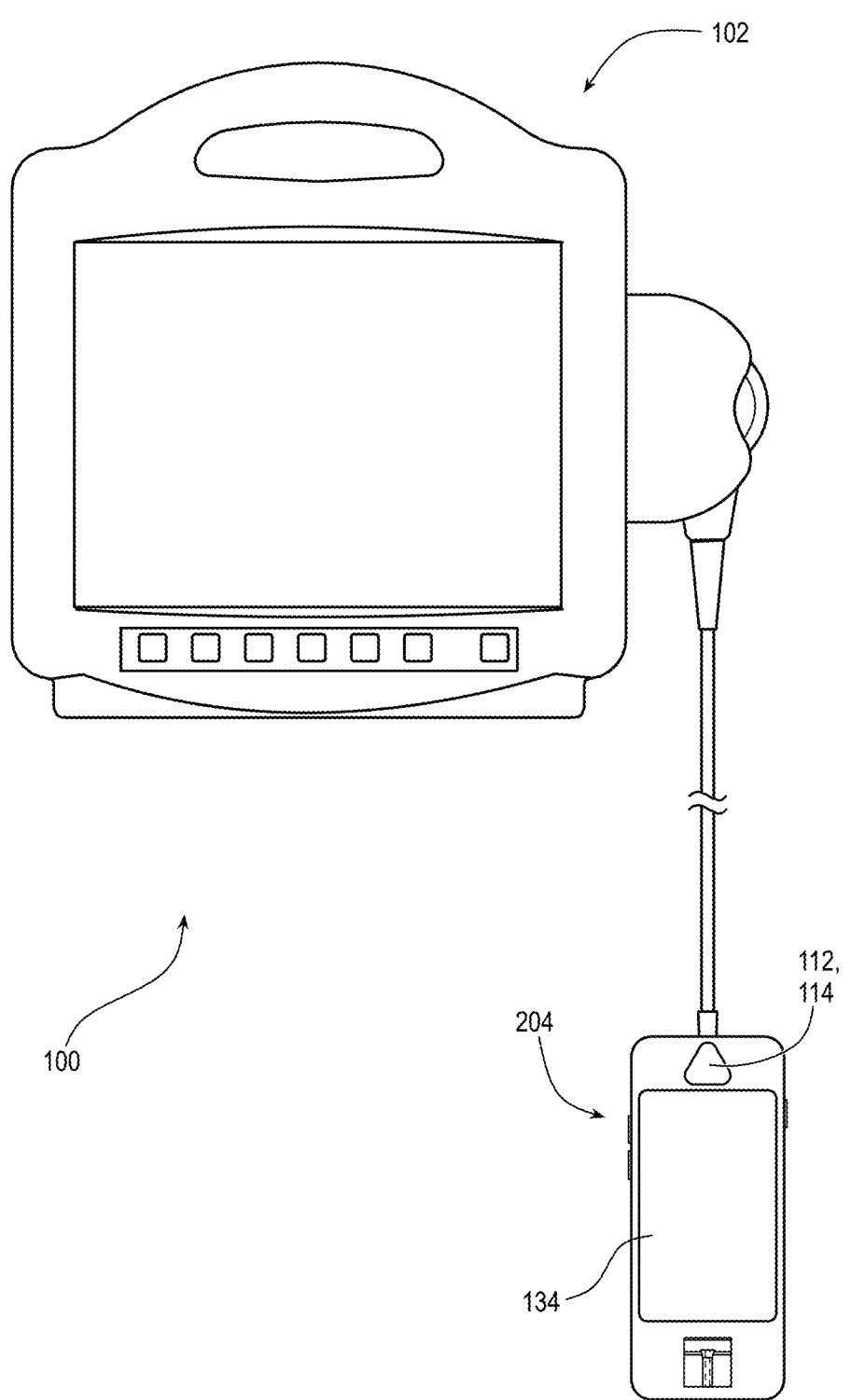
FIG. 3 illustrates the ultrasound system with a second ultrasound probe in accordance with some embodiments.

FIGS. 1 and 3 illustrate an ultrasound system 100 including a console 102 and either a first ultrasound probe 104 or a second ultrasound probe 204 in accordance with some embodiments.

Figure 2:
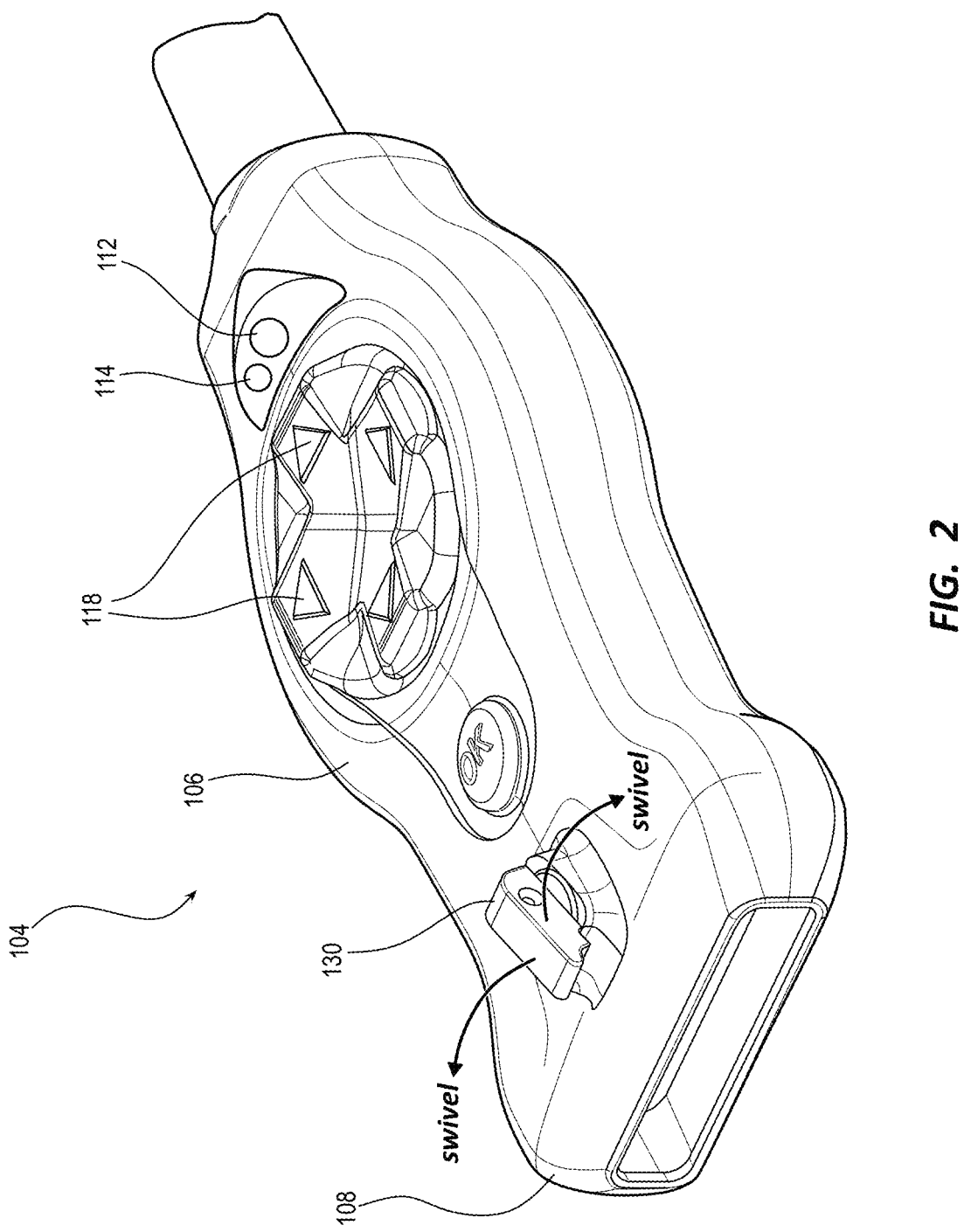
FIG. 2 illustrates a perspective view of the ultrasound probe of FIG. 1 in accordance with some embodiments.

FIG. 2 illustrates a perspective view of the ultrasound probe 104 in accordance with some embodiments.

As shown, the ultrasound probe 104 includes a probe body 106, a probe head 108 extending from a distal end of the probe body 106, and a plurality of ultrasonic transducers 110 arranged in an array in the probe head 108.

The ultrasound probe 104 can also include a camera 112 integrated into a side of the ultrasound probe 104, a light-pattern projector 114 (e.g., a laser light-pattern projector) integrated into the side of the ultrasound probe 104, or both the camera 112 and the light-pattern projector 114 integrated into the side of the ultrasound probe 104. Notably, the side of the ultrasound probe 104 including the camera 112 or the light-pattern projector 114 is shown in FIG. 2 as a major side of the ultrasound probe 104, specifically a top side (or front face) of the ultrasound probe 104, which is convenient for an out-of-plane view of a needle 116 (see FIG. 6) when establishing an insertion site with the needle 116 as set forth in the method below. In addition, the foregoing side of the ultrasound probe 104 conveniently includes various buttons 118 of the ultrasound probe 104 useful for operating the ultrasound probe 104 or 204 or the ultrasound system 100 while establishing an insertion site with the needle 116. That said, the side of the ultrasound probe 104 including the camera 112 or the light-pattern projector 114 can alternatively be a minor side of the ultrasound probe 104, which is convenient for an in-plane view of the needle 116 when establishing an insertion site with the needle 116 as set forth in the method below.

The camera 112 is configured for recording one or more still or moving images 120 (see FIGS. 10 and 11) of a procedural field including a subject portion of a patient therein with a depth of field including a plane of a distal end of the probe head 108 and a field of view including a spatial region about the probe head 108. As set forth in more detail below, the one-or-more still or moving images 120 can be rendered on the display screen of the display 158 along with the ultrasound images 136 associated therewith, which allows a clinician to sustain spatial attention on the display 158 when establishing an insertion site with the needle 116, thereby obviating the clinician from frequently switching his or her spatial attention between the display 158 and the procedural field as done with existing ultrasound systems.

The light-pattern projector 114 is configured to project a light pattern 122 in the spatial region about the probe head 108 focused in the plane of the distal end of the probe head 108, thereby including the foregoing subject portion of the patient in the procedural field. The light pattern 122 is configured for guided insertion of the needle 116 into an anatomical target under the probe head 108 in the procedural field. Similar to the one-or-more still or moving images 120 when rendered on the display screen of the display 158, the light pattern 122 when projected in the spatial region about the probe head 108 allows a clinician to sustain spatial attention in the procedural field when establishing an insertion site with the needle 116 as set forth in the method below, thereby obviating the clinician from frequently switching his or her spatial attention between the procedural field and the display 158 as done with existing ultrasound systems.

Figures 7, 8:
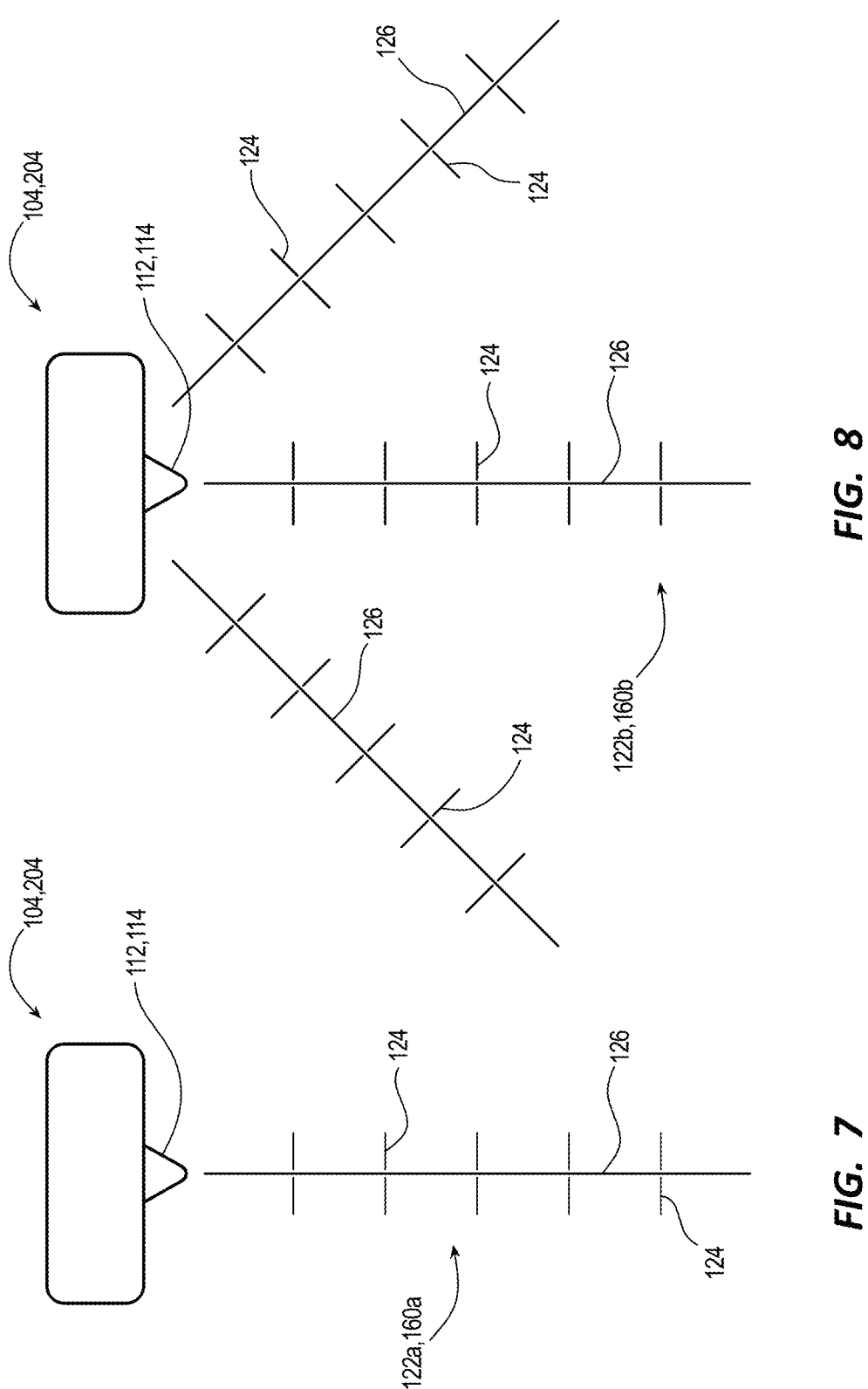
FIG. 7 illustrates a schematic of a first light pattern or first overlying pattern in accordance with some embodiments.
FIG. 8 illustrates a schematic of a second light pattern or a second overlying pattern in accordance with some embodiments.

FIG. 7 illustrates a schematic of a first light pattern 122a in accordance with some embodiments. FIG. 8 illustrates a schematic of a second light pattern 122b in accordance with some embodiments. Notably, when referring to a generic light pattern herein, the light pattern 122 is referenced. When referring to a specific light pattern herein, the light pattern 122a, 122b, or the like is referenced.

Figure 6:
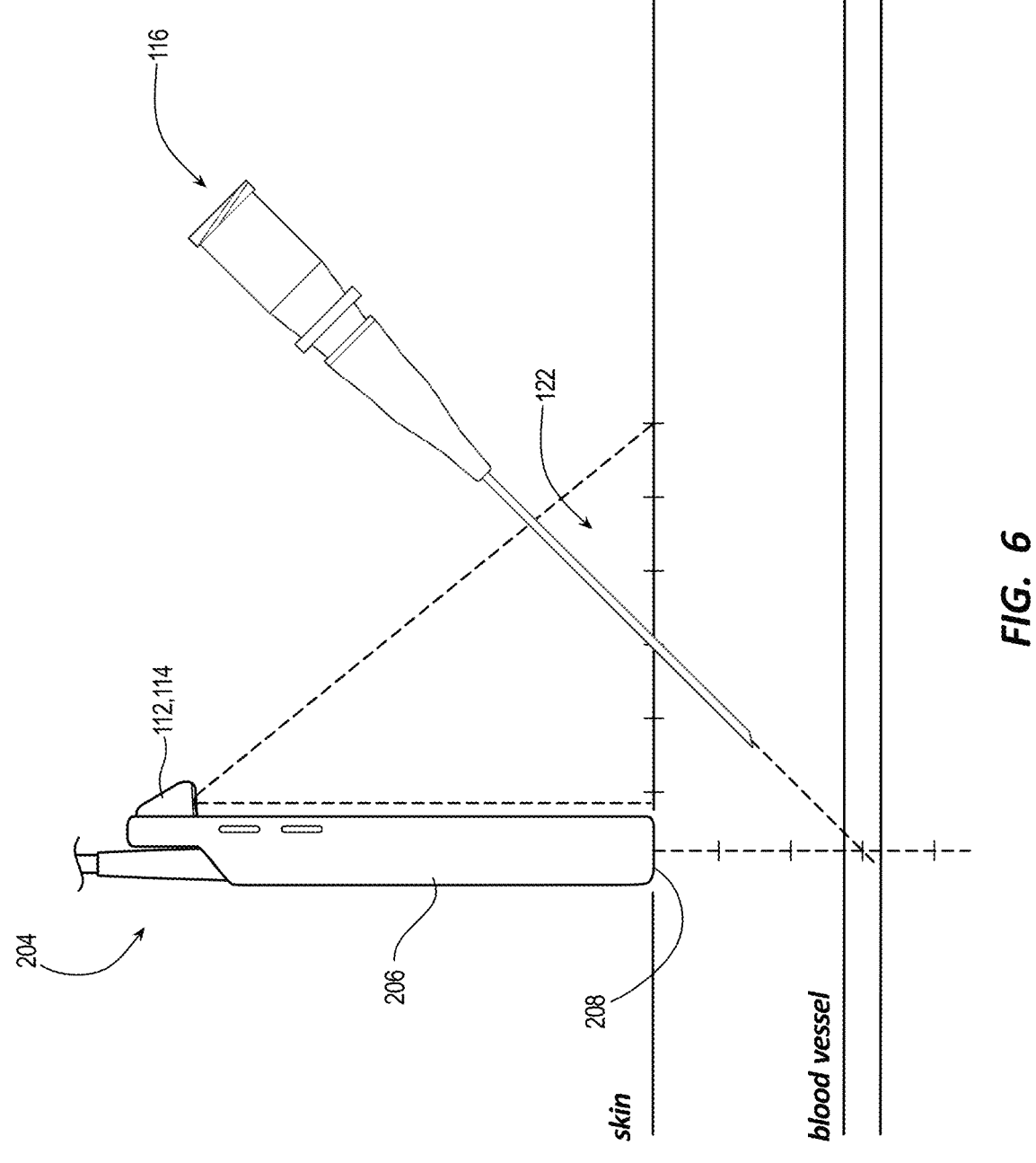
FIG. 6 illustrates a schematic of guided insertion of a needle into an anatomical target with a light pattern projected in a procedural field in accordance with some embodiments.

As shown, the light pattern 122a of 122b includes periodic hash marks 124 along one or more rays 126 radiating from a central axis of the ultrasound probe 104 in the plane of the probe head 108. Indeed, the light pattern 122a includes the hash marks 124 along one ray 126 radiating from the central axis of the ultrasound probe 104, whereas the light pattern 122b includes the hash marks 124 along three rays 126 radiating from the central axis of the ultrasound probe 104. As shown in FIG. 6, each hash mark of the hash marks 124 corresponds to a depth under the probe head 108 accessible by the needle 116 along an associated ray 126 at a needle-insertion angle with respect to the plane of the probe head 108.

Figure 9:
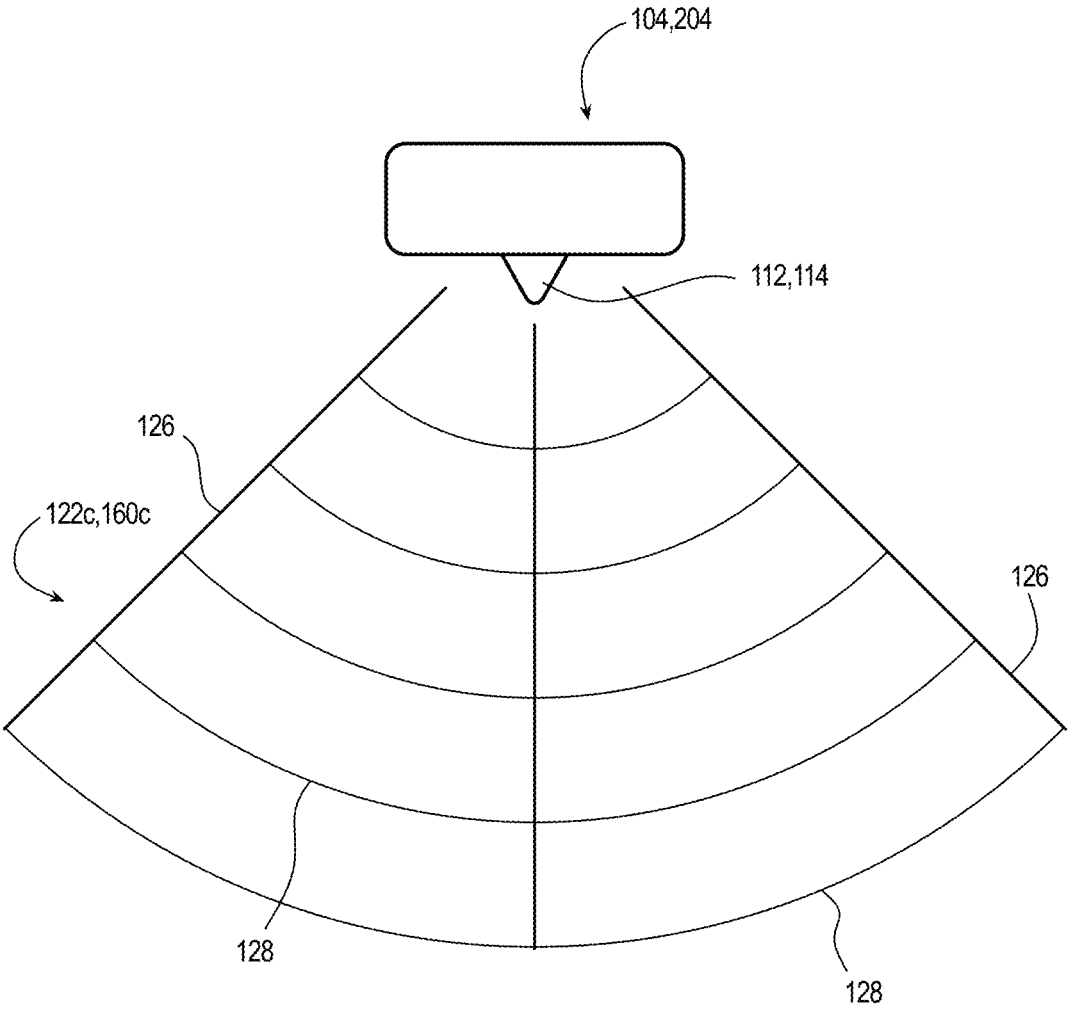
FIG. 9 illustrates a schematic of a third light pattern or a third overlying pattern in accordance with some embodiments.

FIG. 9 illustrates a schematic of a third light pattern 122c in accordance with some embodiments.

As shown, the light pattern 122c includes periodic concentric circular arcs 128 bound between two or more rays 126 radiating from the central axis of the ultrasound probe 104 in the plane of the probe head 108. Indeed, the light pattern 122c includes the circular arcs 128 bound between three rays 126 radiating from the central axis of the ultrasound probe 104. As shown in FIG. 6, each circular arc of the circular arcs 128 corresponds to a depth under the probe head 108 accessible by the needle 116 along an associated ray 126 at a needle-insertion angle with respect to the plane of the probe head 108. Notably, the associated ray 126 can be an intervening ray between the two-or-more rays 126 of the light pattern 122c radiating from the central axis of the ultrasound probe 104. The intervening ray need not be a visible ray of the light pattern 122c; the intervening ray can be envisioned between the two-or-more rays 126 of the light pattern 122c and followed with the needle 116 when establishing an insertion site therewith as set forth in the method below.

The ultrasound probe 104 can also include a needle-guide holder 130 extending from the side of the probe head 108 in common with the side of the ultrasound probe 104 including the camera 112, whether the foregoing side is the major or minor side of the ultrasound probe 104 including the camera 112 or the light-pattern projector 114.

The ultrasound probe 104 can also include a single-use needle guide 132 configured to couple to the needle-guide holder 130. The needle guide 132, the needle-guide holder 130, or a combination of the needle guide 132 and the needle-guide holder 130 can include at least one degree of freedom enabling the needle guide 132 to swivel between sides of the ultrasound probe 104. Indeed, the needle guide 132 can swivel between minor sides of the ultrasound probe 104 if the needle-guide holder 130 extends from a major side of the ultrasound probe 104. The needle guide 132 can alternatively swivel between major sides of the ultrasound probe 104 if the needle-guide holder 130 extends from a minor side of the ultrasound probe 104. To enable the needle guide 132 to swivel between the foregoing sides of the ultrasound probe 104, the needle guide 132 and the needle-guide holder 130 can include a joint (e.g., ball joint) formed therebetween that provides the degree of freedom needed. If the needle guide 132 is used with the needle 116 to establish an insertion site, the needle guide 132 can be advantageously swiveled along each circular arc of the circular arcs 128 of the light pattern 122c. The needle 116 can be subsequently inserted along any existing or envisioned ray of the light pattern 122c to establish an insertion site.

Figures 4, 5:
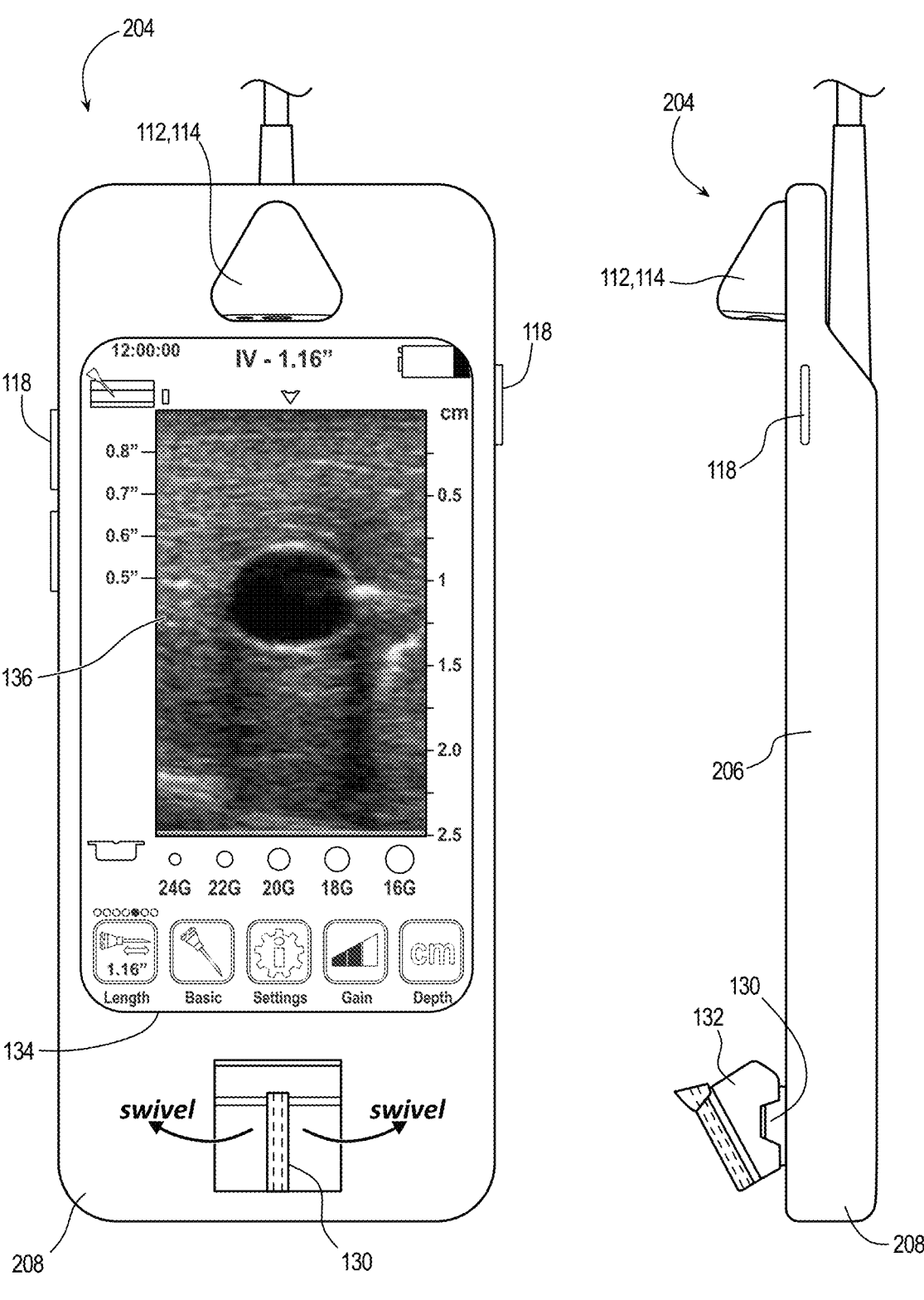
FIG. 4 illustrates a front view of the ultrasound probe of FIG. 3 in accordance with some embodiments.
FIG. 5 illustrates a side view of the ultrasound probe of FIG. 3 in accordance with some embodiments.

FIGS. 4 and 5 illustrate different views of the ultrasound probe 204 in accordance with some embodiments.

As shown, the ultrasound probe 204 includes a probe body 206, a probe head 208 extending from a distal end of the probe body 206, and the plurality of ultrasonic transducers 110 arranged in an array in the probe head 208. In addition, the ultrasound probe 204 can include the camera 112 integrated into a side of the ultrasound probe 204, the light-pattern projector 114 integrated into the side of the ultrasound probe 204, or both the camera 112 and the light-pattern projector 114 integrated into the side of the ultrasound probe 204. As such, the ultrasound probe 204 is like the ultrasound probe 104 in certain ways. Therefore, the description set forth above for the ultrasound probe 104 likewise applies to the ultrasound probe 204.

The ultrasound probe 204 also includes a display 134 integrated into the side of the ultrasound probe 204, specifically the top side (or front face) of the ultrasound probe 204, which differentiates the ultrasound probe 204 from the ultrasound probe 104. The display 134 is configured to render ultrasound images 136 on a display screen thereof, which allows a clinician to sustain spatial attention in the procedural field when establishing an insertion site with the needle 116 as set forth in the method below, thereby obviating the clinician from frequently switching his or her spatial attention between the procedural field, which includes the display 134, and another display (e.g., the display 158 of the console 102) as done with existing ultrasound systems. In addition, the display 134 is configured to render one or more overlying needle trajectories 138 over the ultrasound images 136. (See, for example, FIG. 11 for the one-or-more needle trajectories 138.) The one-or-more needle trajectories 138 are configured for guided insertion of the needle 116 into an anatomical target under the probe head 208 on the display 134. Indeed, the one-or-more needle trajectories 138 are in accordance with one or more depths accessible by the needle 116 as indicated by the light pattern 122.

Notably, the ultrasound probe 104 or 204 can include magnetic sensors to enhance guided insertion of the needle 116 into an anatomical target as set forth herein with magnetic-based needle guidance. Such magnetic-based needle guidance is disclosed in U.S. Pat. Nos. 8,388,541; 8,781,555; 8,849,382; 9,456,766; 9,492,097; 9,521,961; 9,554,716; 9,636,031; 9,649,048; 10,449,330; 10,524,691; and 10,751,509, each of which is incorporated by reference in its entirety into this application.

Figure 12:
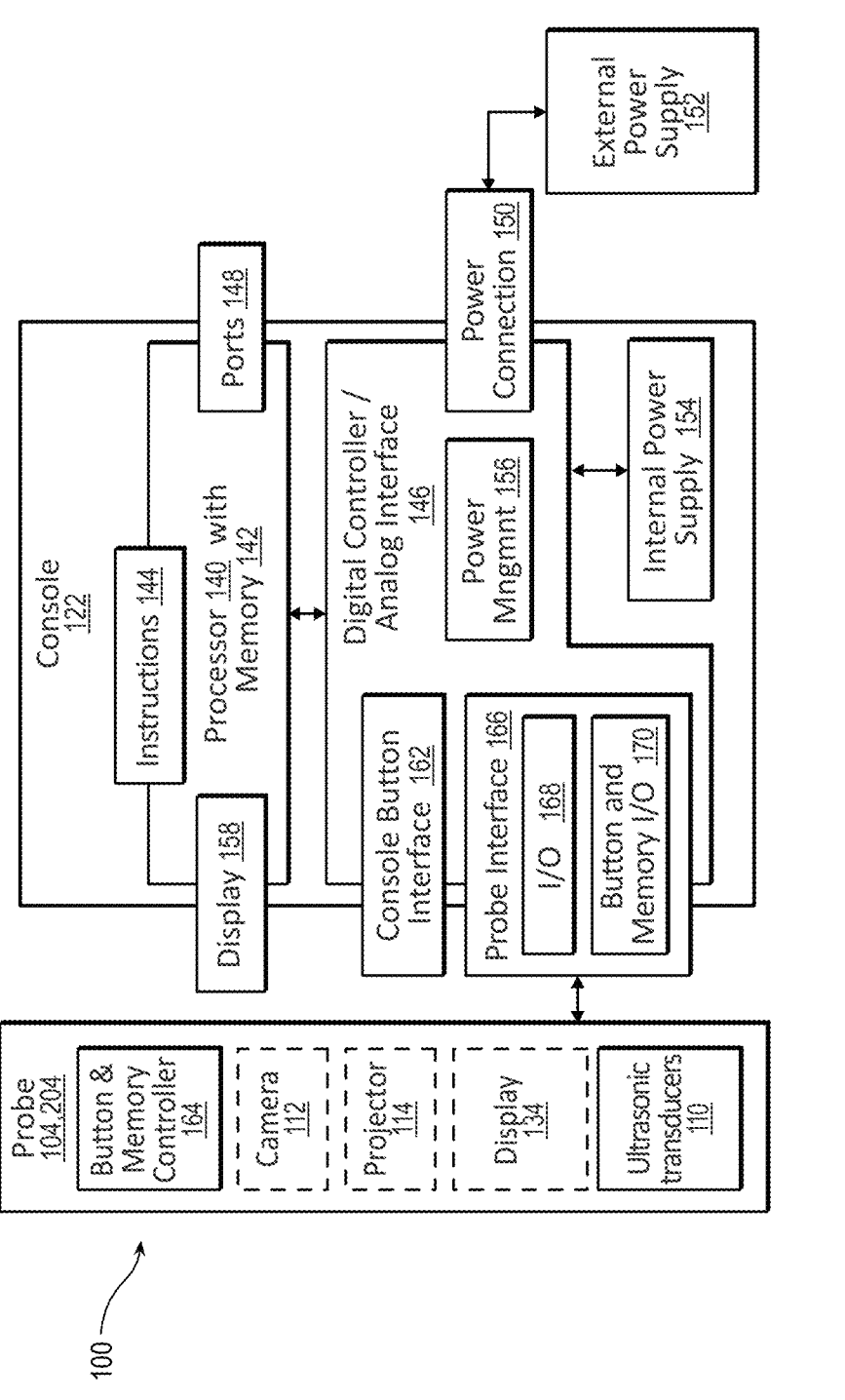
FIG. 12 illustrates a block diagram of the ultrasound system in accordance with some embodiments.

FIG. 12 illustrates a block diagram of the ultrasound system 100 in accordance with some embodiments.

As shown, the console 102 includes a variety of components including a processor 140 and memory 142 such as random-access memory ("RAM") or non-volatile memory (e.g., electrically erasable programmable read-only memory ["EEPROM"]) for controlling various functions of the ultrasound system 100 during operation thereof. Indeed, the console 102 is configured to instantiate by way of executable instructions 144 stored in the memory 142 and executed by the processor 140 various processes for controlling the various functions of the ultrasound system 100.

As to the various processes for controlling the various functions of the ultrasound system 100, the various processes can include beamforming by way of a beamformer configured to drive the ultrasonic transducers 110, wherein driving the ultrasonic transducers 110 includes emitting generated ultrasound signals as well as receiving, amplifying, and digitizing reflected ultrasound signals; signal processing by way of a signal processor configured to detect an amplitude of each of the foregoing reflected ultrasound signals or the digitized signals corresponding thereto; and image processing by way of an image processor configured to manage storage of detected amplitudes and send the ultrasound images 136 corresponding to collections of the detected amplitudes to the display screen of the display 134 or 158 upon completion of the ultrasound images 136.

Further to the various processes for controlling the various functions of the ultrasound system 100, the various processes can include processing electrical signals corresponding to color and brightness data from an image sensor of the camera 112 of the ultrasound probe 104 or 204 into the one-or-more still or moving images 120; determining depths for various anatomical structures in the ultrasound images 136 by way of delays in time between emitting the generated ultrasound signals from the ultrasonic transducers 110 and receiving the reflected ultrasound signals by the ultrasonic transducers 110; adjusting a scale of the light pattern 122 projected from the light-pattern projector 114 in accordance with both the depths for the various anatomical structures in the ultrasound images 136 and a needle-insertion angle, wherein the needle-insertion angle is selected from a single ultrasound system-defined needle-insertion angle, a clinician-selected needle-insertion angle among various ultrasound system-defined needle-insertion angles, and a dynamic needle-insertion angle determined by way of magnetic-based needle guidance; adjusting a scale of the overlying pattern 160 lying over the one-or-more still or moving images 120 in accordance with both the depths for the various anatomical structures in the ultrasound images 136 and the needle-insertion angle; and adjusting a scale of the one-or-more needle trajectories 138 lying over the ultrasound images 136 in accordance with both the depths for various anatomical structures in the ultrasound images 136 and the needle-insertion angle.

The console 102 also includes a digital controller/analog interface 146 in communication with both the processor 140 and other system components to govern interfacing between the ultrasound probe 104 or 204 and the foregoing system components. Ports 148 are also included in the console 102 for connection with additional system components including optional system components such as a printer, storage media, a keyboard, etc. The ports 148 can be universal serial bus ("USB") ports, though other types of ports can be used for these connections or any other connections shown or described herein.

A power connection 150 is included with the console 102 to enable an operable connection to an external power supply 152. An internal power supply 154 (e.g., a battery) can also be employed either with or exclusive of the external power supply 152. Power management circuitry 156 is included with the digital controller/analog interface 146 of the console 102 to regulate power use and distribution.

A display 158 integrated into the console 102 is configured to render on a display screen thereof a graphical user interface ("GUI"), the ultrasound images 136 attained by the ultrasound probe 104 or 204, the one-or-more still or moving images 120 of the procedural field attained by the camera 112 of the ultrasound probe 104 or 204, an overlying pattern 160 lying over the one-or-more still or moving images 120, the one-or-more needle trajectories 138 lying over the ultrasound images 136, etc. That said, the display 158 can alternatively be separate from the console 102 and communicatively coupled thereto. Regardless, control buttons (see FIGS. 1, 3, 10, and 11) accessed through a console button interface 162 of the console 102 can be used to immediately call up to the display screen a desired mode of the ultrasound system 100 for assisting with an ultrasound-based medical procedure such as that for establishing an insertion site with the needle 116, placing a VAD such as a catheter in a blood vessel of a patient at the insertion site, or the like. For example, a mode of the ultrasound system 100 for establishing an insertion site with the needle 116 can include rendering the one-or-more still or moving images 120 of the procedural field, the overlying pattern 160 lying over the one-or-more still or moving images 120, the one-or-more needle trajectories 138 lying over the ultrasound images 136, or a combination thereof.

Figure 10:
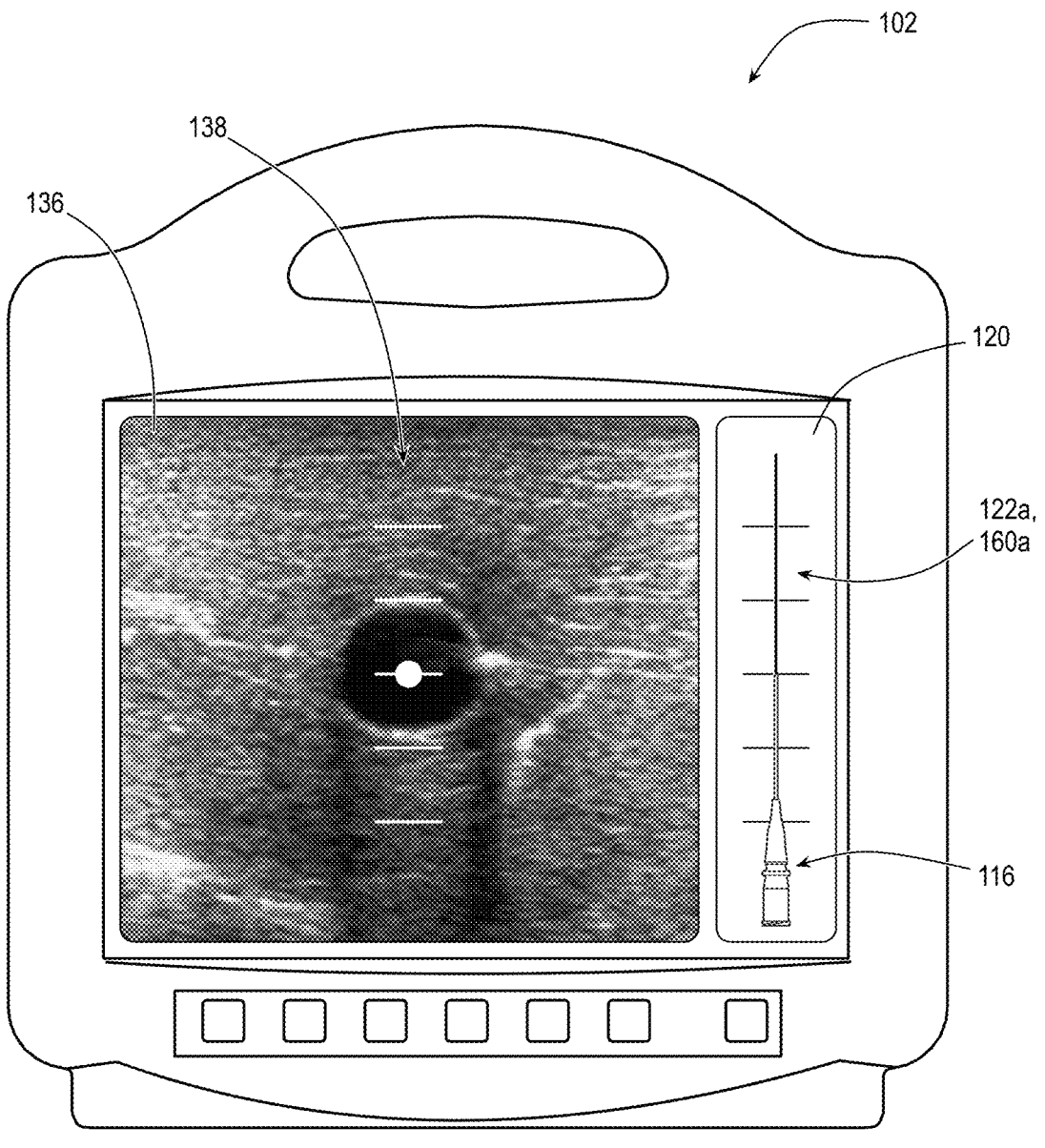
FIG. 10 illustrates guided insertion of a needle into an anatomical target with the first light pattern or the first overlying pattern over one or more still or moving images on a display in accordance with some embodiments.
Figure 11:
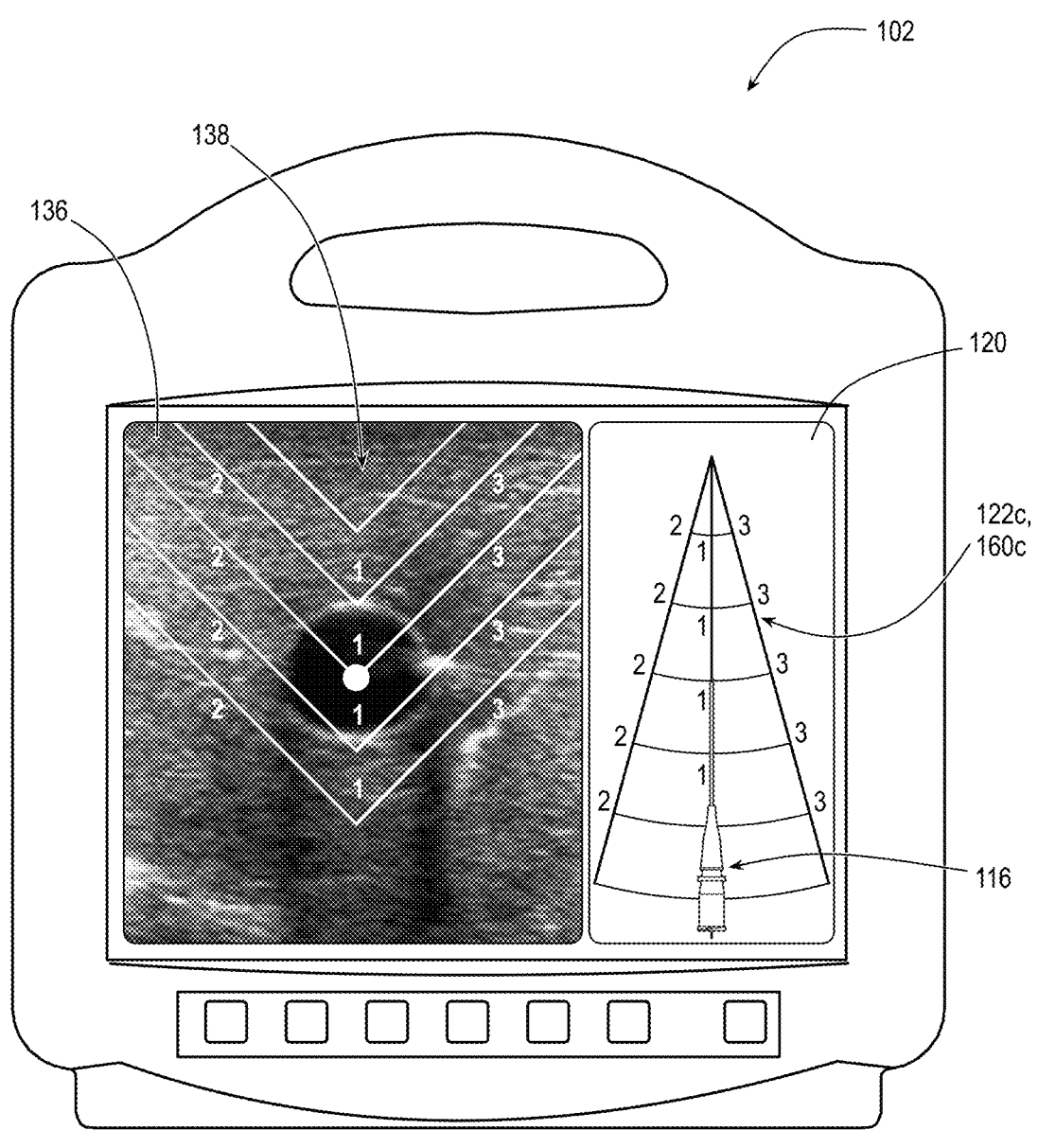
FIG. 11 illustrates guided insertion of a needle into an anatomical target with the third light pattern or the third overlying pattern over the one-or-more still or moving images on the display in accordance with some embodiments.

FIGS. 10 and 11 illustrate guided insertion of the needle 116 into an anatomical target of an ultrasound image with the light pattern 122, specifically the light pattern 122a and 122c, respectively, as shown in the one-or-more still or moving images 120 adjacent the ultrasound image on the display 158.

When rendered on the display screen, the one-or-more still or moving images 120 show at least the needle 116 when the needle 116 is present in the spatial region about the probe head 108 or 208, which, even alone, allows a clinician to sustain spatial attention on the display 158 when establishing an insertion site with the needle 116. If the ultrasound probe 104 or 204 includes the light-pattern projector 114, however, the one-or-more still or moving images 120 can show both the light pattern 122 in the spatial region about the probe head 108 or 208 and the needle 116 in relation to the light pattern 122 for guided insertion of the needle 116 into an anatomical target under the probe head 108 or 208 on the display 158. Having both the light pattern 122 and the needle 116 shown in the one-or-more still or moving images 120 further allows a clinician to sustain spatial attention on the display 158 when establishing the insertion site with the needle 116, thereby obviating the clinician from frequently switching his or her spatial attention between the display 158 and the procedural field as done with existing ultrasound systems.

FIGS. 10 and 11 also illustrate guided insertion of the needle 116 into an anatomical target of an ultrasound image respectively with the overlying pattern 160, specifically the overlying pattern 160a and 160c, respectively, over the one-or-more still or moving images 120 adjacent the ultrasound image on the display 158.

Following on the foregoing, if the ultrasound probe 104 or 204 does not include the light-pattern projector 114, or if a clinician prefers not to use the light-pattern projector 114 of the ultrasound probe 104 or 204, the one-or-more still or moving images 120 can show the overlying pattern 160 lying thereover. When the needle 116 is present in the spatial region about the probe head 108 or 208, the one-or-more still or moving images 120 can thusly show both the overlying pattern 160 and the needle 116 in relation to the overlying pattern 160 for guided insertion of the needle 116 into an anatomical target under the probe head 108 or 208 on the display 158. Having both the overlying pattern 160 and the needle 116 shown in the one-or-more still or moving images 120 further allows a clinician to sustain spatial attention on the display 158 when establishing the insertion site with the needle 116, thereby obviating the clinician from frequently switching his or her spatial attention between the display 158 and the procedural field as done with existing ultrasound systems.

Like the light pattern 122a or 122b, the overlying pattern 160a or 160b includes the periodic hash marks 124 along one or more rays 126 radiating from the central axis of the ultrasound probe 104 or 204 in the plane of the probe head 108 or 208; however, unlike the light pattern 122*a* or 122*b*, the hash marks 124 and the one-or-more rays 126 are virtual, existing only on the display screen. By analogy to the light pattern 122*a*, the overlying pattern 160*a* likewise includes the hash marks 124 along one ray 126 radiating from the central axis of the ultrasound probe 104 or 204, and, by analogy to the light pattern 122*b*, the overlying pattern 160*b* likewise includes the hash marks 124 along three rays 126 radiating from the central axis of the ultrasound probe 104 or 204. Each hash mark of the hash marks 124 corresponds to a depth under the probe head 108 or 208 accessible by the needle 116 along an associated ray 126 at a needle-insertion angle with respect to the plane of the probe head 108 or 208.

Like the light pattern 122*c*, the overlying pattern 160*c* includes periodic concentric circular arcs 128 bound between two or more rays 126 radiating from a central axis of the ultrasound probe 104 or 204 in the plane of the probe head 108 or 208; however, unlike the light pattern 122*c*, the circular arcs 128 and the two-or-more rays 126 are virtual, existing only on the display screen. By analogy to the light pattern 122*c*, the overlying pattern 160*c* likewise includes the circular arcs 128 bound between three rays 126 radiating from the central axis of the ultrasound probe 104 or 204. Each circular arc of the circular arcs 128 corresponds to a depth under the probe head 108 or 208 accessible by the needle 116 along an associated ray 126 at a needle-insertion angle with respect to the plane of the probe head 108 or 208. Notably, the associated ray 126 can be an intervening ray between the two-or-more rays 126 of the overlying pattern 160*c* radiating from the central axis of the ultrasound probe 104 or 204. The intervening ray need not be a visible ray of the overlying pattern 160*c*; the intervening ray can be envisioned between the two-or-more rays 126 of the overlying pattern 160*c* and followed with the needle 116 when establishing an insertion site therewith as set forth in the method below.

As set forth above, the display 158 is configured to render on the display screen thereof the one-or-more needle trajectories 138 lying over the ultrasound images 136. The one-or-more needle trajectories 138 are configured for guided insertion of the needle 116 into an anatomical target under the probe head 108 or 208 on the display 158. Indeed, as shown in FIG. 11, the one-or-more needle trajectories 138 are in accordance with one or more depths accessible by the needle 116 indicated by the light pattern 122*c* or the overlying pattern 160*c*.

The needle trajectories 138 labeled '1' in FIG. 11 are straightforwardly understood as being in a plane perpendicular to that of an ultrasound beam for a so called out-of-plane view with respect to the needle 116. Moving the needle 116 from circular arc 128 to circular arc 128 of the light pattern 122*c* or overlying pattern 160*c* of FIG. 11 toward the central axis of the ultrasound probe 104 or 204 while keeping the needle-insertion angle constant moves the needle 116 from trajectory to trajectory of the one-or-more needle trajectories 138 in a same direction (e.g., up) on the display screen. Indeed, inserting the needle 116 into a patient at the circular arc 128 nearest the central axis of the ultrasound probe 104 or 204 results in overshooting an anatomical target, for example, a blood vessel under the probe head 108 or 208. Notably, the needle 116 could still access the blood vessel but distal of the probe head 108 or 208. Similarly, moving the needle 116 from circular arc 128 to circular arc 128 of the light pattern 122*c* or overlying pattern 160*c* of FIG. 11 away from the central axis of the ultrasound probe 104 or 204 while keeping the needle-insertion angle constant moves the needle 116 from trajectory to trajectory of the one-or-more needle trajectories 138 in a same direction (e.g., down) on the display screen. Indeed, inserting the needle 116 into the patient at the circular arc 128 farthest from the central axis of the ultrasound probe 104 or 204 results in undershooting the blood vessel under the probe head 108 or 208. Notably, the needle 116 would still access the blood vessel but proximal of the probe head 108 or 208 and, ultimately, through a backwall of the blood vessel if the needle trajectory is completely followed.

The needle trajectories 138 labeled '2' and '3' in of FIG. 11 are in mirrored planes oblique to that of the ultrasound beam, and, as such, approach the blood vessel obliquely. However, like that set forth for the needle trajectories 138 labeled '1' in FIG. 11, moving the needle 116 from circular arc 128 to circular arc 128 of the light pattern 122*c* or overlying pattern 160*c* of FIG. 11 toward the central axis of the ultrasound probe 104 or 204 while keeping the needle-insertion angle constant moves the needle 116 from trajectory to trajectory of the one-or-more needle trajectories 138 in a same direction (e.g., up) on the display screen. Moving the needle 116 from circular arc 128 to circular arc 128 of the light pattern 122*c* or overlying pattern 160*c* of FIG. 11 away from the central axis of the ultrasound probe 104 or 204 while keeping the needle-insertion angle constant moves the needle 116 from trajectory to trajectory of the one-or-more needle trajectories 138 in a same direction (e.g., down) on the display screen.

Adverting briefly back to the ultrasound probe 104 or 204, the ultrasound probe 104 or 204 includes the buttons 118 for operating the ultrasound probe 104 or 204 or the ultrasound system 100 of which the ultrasound probe 104 or 204 is part. For example, the buttons 118 can be configured for selecting a desired mode of the ultrasound system 100 as set forth above. The ultrasound probe 104 or 204 includes a button-and-memory controller 164 configured for operable communication with a probe interface 166 of the console 102, which probe interface 166 includes an input/output ("I/O") component 168 for interfacing with the ultrasonic transducers 110 and a button-and-memory I/O component 170 for interfacing with the button-and-memory controller 164.
Methods Methods include a method of using the ultrasound system 100 to establish an insertion site for access to an anatomical structure (e.g., blood vessel) of a patient. The method includes one or more steps selected from an ultrasound probe-obtaining step, an ultrasound probe-moving step, a recording step, an ultrasound image-monitoring step, a needle guide-attaching step, a needle guide-swiveling step, and a needle-inserting step.

The ultrasound probe-obtaining step includes obtaining the ultrasound probe 104. As set forth above, the ultrasound probe 104 includes the probe body 106, the probe head 108 extending from the distal end of the probe body 106, and the camera 112 integrated into the side of the ultrasound probe 104.

The needle guide-attaching step includes attaching the needle guide 132 to the needle-guide holder 130 extending from the probe body 106. The needle guide 132 includes a needle through hole configured to direct the needle 116 into the patient under the probe head 108 at the needle-insertion angle defined by the needle guide 132.

The ultrasound probe-moving step includes moving the ultrasound probe 104 over the patient while the ultrasound probe 104 emits generated ultrasound signals into the patient from the ultrasonic transducers 110 in the probe head 108 and receives reflected ultrasound signals from the patient by the ultrasonic transducers 110.

The recording step includes recording the one-or-more still or moving images 120 of the procedural field including a subject portion of the patient therein. As set forth above, the one-or-more still or moving images 120 are recorded with a depth of field including the plane of the distal end of the probe head 108 and the field of view including the spatial region about the probe head 108.

The ultrasound image-monitoring step includes monitoring ultrasound images 136 rendered on the display screen of the display 158 associated with the console 102 of the ultrasound system 100 to identify an anatomical target of the patient under the probe head 108.

The needle guide-swiveling step includes swiveling the needle guide 132 between sides of the ultrasound probe 104 to find a suitable needle trajectory before the needle-inserting step. The needle-guide holder 130, the needle guide 132, or a combination of the needle-guide holder 130 and the needle guide 132 such as the joint formed therebetween includes at least one degree of freedom enabling the swiveling of the needle guide 132.

The needle-inserting step includes inserting the needle 116 into the anatomical target. The inserting of the needle 116 into the anatomical target during the needle-inserting step is guided in the procedural field with reference to the light pattern 122 in the spatial region about the probe head 108, on the display 158 with reference to the one-or-more still or moving images 120 or the one-or-more needle trajectories 138 rendered on the display screen thereof, or a combination thereof.

As to guidance in the procedural field with reference to the light pattern 122, the light pattern 122 is projected into the spatial region about the probe head 108 from the light-pattern projector 114 and focused in the plane of the distal end of the probe head 108 for guiding the needle 116 in the procedural field. As set forth above, the light pattern 122a or 122b includes the periodic hash marks 124 along the one-or-more rays 126 radiating from the central axis of the ultrasound probe 104 in the plane of the probe head 108. Each hash mark of the hash marks 124 corresponds to a depth under the probe head 108 accessible by the needle 116 along an associated ray 126 at a needle-insertion angle with respect to the plane of the probe head 108. As further set forth above, the light pattern 122c includes the periodic concentric circular arcs 128 bound between the two-or-more rays 126 radiating from the central axis of the ultrasound probe 104 in the plane of the probe head 108. Each circular arc of the circular arcs 128 corresponds to a depth under the probe head 108 accessible by the needle 116 along an associated ray 126 at a needle-insertion angle with respect to the plane of the probe head 108.

As to guidance on the display 158 with reference to the one-or-more still or moving images 120, the one-or-more still or moving images 120 can show both the light pattern 122 in the spatial region about the probe head 108 and the needle 116 in relation to the light pattern 122 for guiding the needle 116 on the display 158. However, if the ultrasound probe 104 does not include the light-pattern projector 114, or if a clinician prefers not to use the light-pattern projector 114 of the ultrasound probe 104, the one-or-more still or moving images 120 can show the overlying pattern 160 lying thereover for guiding the needle 116 on the display 158. As set forth above, the overlying pattern 160a or 160b includes the periodic hash marks 124 along the one-or-more rays 126 radiating from the central axis of the ultrasound probe 1014 in the plane of the probe head 108. Each hash mark of the hash marks 124 corresponds to a depth under the probe head 108 accessible by the needle 116 along an associated ray 126 at a needle-insertion angle with respect to the plane of the probe head 108. As further set forth above, the overlying pattern 160c includes the periodic concentric circular arcs 128 bound between the two-or-more rays 126 radiating from the central axis of the ultrasound probe 104 in the plane of the probe head 108. Each circular arc of the circular arcs 128 corresponds to a depth under the probe head 108 accessible by the needle 116 along an associated ray 126 at a needle-insertion angle with respect to the plane of the probe head 108.

Further as to guidance on the display 158 with reference to the one-or-more needle trajectories 138, the ultrasound images 136 can show the one-or-more needle trajectories 138 in accordance with one or more depths accessible by the needle 116 indicated by the light pattern 122 or overlying pattern 160 in the one-or-more still or moving images 120 for guiding the needle 116 on the display 158.

Notably, the foregoing method involves the ultrasound probe 104; however, the method can be modified for the ultrasound probe 204. In such a method, the ultrasound images 136 are displayed on the display 134 of the ultrasound probe 204, optionally, in combination with the ultrasound images 136 and the one-or-more still or moving images 120 on the display 158 of the console 102. As set forth above, displaying the images on the display 134 of the ultrasound probe 204 allows a clinician to sustain spatial attention in the procedural field when establishing the insertion site with the needle 116 in the needle-inserting step, thereby obviating the clinician from frequently switching his or her spatial attention between the procedural field, which includes the display 134, and another display (e.g., the display 158 of the console 102) as done with existing ultrasound systems.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. An ultrasound probe, comprising:
a display screen on a visible side of the ultrasound probe, the display screen coupled to ultrasound imaging components in the ultrasound probe, the ultrasound imaging components configured to capture live subcutaneous images and render the live subcutaneous images on the display screen;
one or more needle trajectories depicted on the display screen over the live subcutaneous images, the one or more needle trajectories configured to assist a user in guided insertion of a needle into an anatomical target under the ultrasound probe; and
a light-pattern projector on the visible side of the ultrasound probe adjacent the display screen, the light-pattern projector configured to project a light pattern corresponding to a subcutaneous depth accessible by the needle, wherein the light pattern comprises a plurality of hash marks along a beam of light, each of the plurality of hash marks corresponding to the subcutaneous depth accessible by the needle.

2. The ultrasound probe according to claim 1, further comprising a needle-guide holder on the visible side of the ultrasound probe adjacent the display screen.

3. The ultrasound probe according to claim 2, further comprising a single-use needle guide coupled to the needle-guide holder, the single-use needle guide including at least one degree of freedom enabling the single-use needle guide to swivel.

4. The ultrasound probe according to claim 1, further comprising a camera configured for recording images of a procedural field with a depth of field including a plane of a skin contacting end of the ultrasound probe and a field of view including a spatial region around the skin contacting end of the ultrasound probe.

5. The ultrasound probe according to claim 4, wherein the camera is positioned adjacent the light-pattern projector on the visible side of the ultrasound probe.

6. The ultrasound probe according to claim 4, wherein the images show both the light pattern in the spatial region around the skin contacting end of the ultrasound probe and the needle in relation to the light pattern when both the light pattern and the needle are present in the spatial region around the skin contacting end of the ultrasound probe.

7. The ultrasound probe according to claim 1, further comprising depth markings on each side of the display screen, wherein a first set of depth markings on a first side are marked in inches, and wherein a second set of depth markings on a second side opposite the first side are marked in centimeters.

8. The ultrasound probe according to claim 7, further comprising a selection of needle gauge sizes adjacent the display screen.

9. The ultrasound probe according to claim 8, further comprising a selection of needle lengths adjacent the display screen.

10. The ultrasound probe according to claim 9, further comprising a selection of needle types adjacent the display screen.

11. The ultrasound probe according to claim 10, wherein a selected needle gauge, a selected needle length, and a selected needle type are indicated adjacent the display screen.

12. An ultrasound probe, comprising:

a display screen on a visible side of the ultrasound probe, the display screen coupled to ultrasound imaging components in the ultrasound probe, the ultrasound imaging components configured to capture live subcutaneous images and render the live subcutaneous images on the display screen;

one or more needle trajectories depicted on the display screen over the live subcutaneous images, the one or more needle trajectories configured to assist a user in guided insertion of a needle into an anatomical target under the ultrasound probe; and a light-pattern projector on the visible side of the ultrasound probe adjacent the display screen, the light-pattern projector configured to project a light pattern corresponding to a subcutaneous depth accessible by the needle, wherein the light pattern comprises concentric circular arcs bound between beams of light, each of the concentric circular arcs corresponding to the subcutaneous depth accessible by the needle.

13. The ultrasound probe according to claim 12, wherein the one or more needle trajectories are in accordance with concentric circular arcs.

14. The ultrasound probe according to claim 12, further comprising a needle-guide holder on the visible side of the ultrasound probe adjacent the display screen.

15. The ultrasound probe according to claim 14, further comprising a single-use needle guide coupled to the needle-guide holder, the single-use needle guide including at least one degree of freedom enabling the single-use needle guide to swivel.

16. The ultrasound probe according to claim 12, further comprising a camera configured for recording images of a procedural field with a depth of field including a plane of a skin contacting end of the ultrasound probe and a field of view including a spatial region around the skin contacting end of the ultrasound probe.

17. The ultrasound probe according to claim 16, wherein the camera is positioned adjacent the light-pattern projector on the visible side of the ultrasound probe.

18. The ultrasound probe according to claim 16, wherein the images show both the light pattern in the spatial region around the skin contacting end of the ultrasound probe and the needle in relation to the light pattern when both the light pattern and the needle are present in the spatial region around the skin contacting end of the ultrasound probe.

19. The ultrasound probe according to claim 12, further comprising depth markings on each side of the display screen, wherein a first set of depth markings on a first side are marked in inches, and wherein a second set of depth markings on a second side opposite the first side are marked in centimeters.

20. The ultrasound probe according to claim 19, further comprising a selection of needle gauge sizes adjacent the display screen.

\* \* \* \* \*